(12) United States Patent
Weisbart et al.

(10) Patent No.: US 10,383,945 B2
(45) Date of Patent: Aug. 20, 2019

(54) METHODS FOR DNA-DEPENDENT TARGETING OF A CELL PERMEANT ANTIBODY

(71) Applicant: The United States of America as represented by the Department of Veterans Affairs, Washington, DC (US)

(72) Inventors: Richard H. Weisbart, Sepulveda, CA (US); Robert N. Nishimura, Sepulveda, CA (US)

(73) Assignee: THE UNITED STATES OF AMERICA AS REPRESENTED BY THE DEPARTMENT OF VERTERANS AFFAIRS DC (US)

( * ) Notice: Subject to any disclaimer, the term of this patent is extended or adjusted under 35 U.S.C. 154(b) by 133 days.

(21) Appl. No.: 15/047,575

(22) Filed: Feb. 18, 2016

(65) Prior Publication Data
US 2016/0235859 A1 Aug. 18, 2016

Related U.S. Application Data

(60) Provisional application No. 62/117,694, filed on Feb. 18, 2015.

(51) Int. Cl.
| | |
|---|---|
| A61K 47/68 | (2017.01) |
| C07K 16/18 | (2006.01) |
| A61K 47/48 | (2006.01) |
| C07K 16/44 | (2006.01) |
| A61K 39/00 | (2006.01) |

(52) U.S. Cl.
CPC .... *A61K 47/48538* (2013.01); *A61K 47/6843* (2017.08); *C07K 16/18* (2013.01); *C07K 16/44* (2013.01); *A61K 2039/505* (2013.01); *C07K 2317/622* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 2008/0292618 | A1 | 11/2008 | Weisbart |
| 2013/0266570 | A1 | 10/2013 | Weisbart et al. |
| 2014/0050723 | A1 * | 2/2014 | Hansen .............. C07K 16/44 424/133.1 |
| 2014/0234309 | A1 | 9/2014 | Nishimura et al. |

FOREIGN PATENT DOCUMENTS

| | | | |
|---|---|---|---|
| WO | WO2010/138769 A1 | 12/2010 | |
| WO | WO2010/148010 A1 | 12/2010 | |
| WO | WO 2012/135831 | * 10/2012 | |
| WO | WO 2014/087023 | * 6/2014 | |

OTHER PUBLICATIONS

Swystun et al (Journal of Thrombosis ad Haematostasis, 2011, 9:2313-2321).*
Ruiz-Argüelles A, Pérez-romano B, Llorente L, Alarcón-Segovia D, Castellanos JM. "Penetration of anti-DNA antibodies into immature live cells." *J Autoimmun*, Oct. 1998;11(5):547-556—Exhibit 10.
Song YC, Sun GH, Lee TP, Huang JC, Yu CL, Chen CH, Tang SJ, and Sun KH (2008) "Arginines in the CDR of anti-dsDNA autoantibodies facilitate cell internalization via electrostatic interactions." *Eur. J. Immunol*. 38(11):3178-90—Exhibit 11.
Vlahakos D, Foster MH, Ucci AA, Barrett KJ, Datta SK, and Madaio MP (1992) "Murine monoclonal anti-DNA antibodies penetrate cells, bind to nuclei, and induce glomerular proliferation and proteinuria in vivo." *J. Am. Soc. Nephrol*. 2(8):1345-54—Exhibit 12.
Weidle Ulrich H., Maisel Daniela, Brinkmann Ulrich, Tiefenthaler Georg, "The Translational Potential for Target Validation and Therapy Using Intracellular Antibodies in Oncology," *Cancer Genomics & Proteomics* 10: 239-250 (2013)—Exhibit 13.
Weisbart Richard H., Gera Joseph F., Chan Grace, Hansen James E., Li Erica, Cloninger Cheri, Levine Arnold J., and Nishimura Robert N. "A Cell-Penetrating Bispecific Antibody for Therapeutic Regulation of Intracellular Targets", *Therapeutic Discovery, Molecular Cancer Therapeutics*, 11(10) Oct. 2012; 2012 American Association for Cancer Research, pp. 2169-2173—Exhibit 14.
Weisbart Richard H., Chan Grace, Jordaan Gwen, Noble Philip W., Liu Yanfeng, Glazer Peter M., Nishimura Robert N., & Hansen James E., "DNA-dependent targeting of cell nuclei by a lupus autoantibody", *Scientific Reports* | 5:12022 | DOI: 10.1038/srep12022, pp. 1-6—Exhibit 15.
Weisbart R H, Noritake D T, Wong A L, Chan G, Kacena A, and Colburn K K, "A conserved anti-DNA antibody idiotype associated with nephritis in murine and human systemic lupus erythematosus" J Immunol 1990; 144:2653-2658—Exhibit 16 and.
Zack D J, Yamamoto K, Wong A L, Stempniak M, French C and Weisbart R H, "DNA mimics a self-protein that may be a target for some anti-DNA antibodies in systemic lupus erythematosus." *J Immunol* 1995; 154:1987-1994—Exhibit 17.
Avrameas A, Ternynck T, Nato F, Buttin G, and Avrameas S (1998) "Polyreactive anti-DNA monoclonal antibodies and a derived peptide as vectors for the intracytoplasmic and intranuclear translocation of macromolecules" *Proc. Natl. Acad. Sci. U.S.A*. 95(10):5601-5606—Exhibit 7.

(Continued)

*Primary Examiner* — Laura B Goddard
(74) *Attorney, Agent, or Firm* — Ballard Spahr LLP

(57) ABSTRACT

The invention provides methods for selective targeting of live cells, which have undergone or are undergoing radiation or chemotherapy, at a site of interest with a cell-penetrating polypeptide. In one embodiment of the invention, the method comprises contacting the live cells with a cell-penetrating polypeptide comprising cell-penetrating determinants so that the cell-penetrating polypeptide binds extracellular DNA near or around the live cells so as to form a complex or association therewith such that the complex or associated polypeptide-DNA so bound bind the live cells and penetrates the live cells thereby selectively targeting live cells at a site of interest with a cell-penetrating polypeptide.

20 Claims, 3 Drawing Sheets

(56) References Cited

OTHER PUBLICATIONS

Hansen, J. E., Chan, G., Liu, Y., Hegan, D. C., Dalai, S., Dray, E., Kwon, Y., Xu, Y., Xu, X., Peterson-Roth, E., Geiger, E., Gera, J., Sweasy, J. B., Sung, P., Rockwell, S., Nishimura, R. N., Weisbart, R. H., and P, M. G. (2012) Targeting cancer with a lupus autoantibody. *Science translational medicine* 4, 157ra142. doi:10.1126/scitranslmed. 3004385; NIH Public Access, Author Manuscript, pp. 1-14—Exhibit 8.
Noble Philip W., Young Melissa R., Bernatsky Sasha, Weisbart Richard H. & Hansen James E. "A nucleolytic lupus autoantibody is toxic to BRCA2-deficient cancer cells", *Scientific Reports* 4: 5958 DOI: 10.1038/srep05958, pp. 1-4—Exhibit 9.

\* cited by examiner

METHODS FOR DNA-DEPENDENT TARGETING OF A CELL PERMEANT ANTIBODY

The subject application claims the priority of U.S. Ser. No. 62/117,694, filed Feb. 18, 2015, the disclosure of which, in its entirety, is hereby incorporated by reference into this application.

This invention was made with government support by the United States Department of Veterans Affairs. The government has certain rights in the invention.

Throughout this application various publications are referenced. The disclosures of these publications in their entireties are hereby incorporated by reference into this application in order to more fully describe the state of the art to which this invention pertains.

BACKGROUND OF THE INVENTION

A select group of lupus anti-DNA autoantibodies penetrate into living cells (1), and one unusual lupus autoantibody that penetrates cell nuclei without causing any apparent harm to normal cells or tissues, 3E10 (2), has been developed as a molecular delivery vehicle. Specifically, a 3E10 single chain variable fragment (scFv) with an enhancing mutation in CDR1 that increases DNA binding and efficiency of nuclear penetration has been used to carry cargo proteins including p53, Hsp70, and other antibody fragments into cell nuclei in vitro and in vivo (3-6). 3E10 scFv also has activity by itself and has been shown to inhibit DNA repair, sensitize cancer cells to DNA-damaging therapy, and to be toxic to BRCA2-deficient cancer cells (7). 3E10 scFv has potential to be used in molecular therapy approaches to diseases ranging from cancer to ischemic conditions such as stroke, and a greater understanding of the details of the mechanism by which it penetrates cell nuclei is important to further delineating the scope of its therapeutic applications.

Mutations in 3E10 that interfere with its ability to bind DNA also render the antibody incapable of nuclear penetration. In addition, 3E10 scFv has previously been shown capable of penetrating into cell nuclei in an ENT2-dependent manner, with efficiency of nuclear uptake greatly impaired in ENT2-deficient cells (8). Taken together, these findings suggest a link between cellular uptake of DNA and nuclear penetration by 3E10 scFv. Interestingly, when a 3E10 scFv-Hsp70 fusion protein (Fv-Hsp70) was administered intravenously to rats three hours after ligation of middle cerebral arteries to induce stroke, Fv-Hsp70 was found to selectively localize to regions of ischemic brain (9).

The invention involves the discovery of the mechanism by which some anti-DNA antibodies or fragments thereof penetrate the cell for use in better treating disease, disorders and conditions.

SUMMARY OF THE INVENTION

The invention provides methods for selective targeting of live cells, which have undergone or are undergoing radiation or chemotherapy, at a site of interest with a cell-penetrating polypeptide. In one embodiment of the invention, the method comprises contacting the live cells with a cell-penetrating polypeptide comprising cell-penetrating determinants so that the cell-penetrating polypeptide binds extracellular DNA near or around the live cells so as to form a complex or association therewith such that the complex or associated polypeptide-DNA so bound bind the live cells and penetrates the live cells thereby selectively targeting live cells at a site of interest with a cell-penetrating polypeptide.

Additionally, the invention provides method for selective targeting of live cells at or near the proximity of a cellular injury with a cell-penetrating polypeptide which comprises cell-penetrating determinants joined to, or combined with, a therapeutic agent. In one embodiment, the method comprising administering the cell-penetrating polypeptide at or near the proximity of the injury so that it binds extracellular DNA from the cellular injury so as to form a complex or association therewith such that the complex or associated polypeptide-DNA-therapeutic agent so bound bind the live cells and penetrates the live cells thereby selectively targeting live cells at a site of interest with the cell-penetrating polypeptide.

The invention further provides methods for selective targeting of live cells at or near the proximity of a cellular injury with a cell-penetrating polypeptide. In an embodiment of the invention, the cell-penetrating determinants are joined to, or combined with, a therapeutic agent. The method may comprise contacting the live cells with a composition having (a) a cell-penetrating polypeptide which comprises cell-penetrating determinants and (b) extracellular DNA so that the cell-penetrating polypeptide binds extracellular DNA near or around the live cells so as to form a complex or association therewith such that the complex or associated polypeptide-DNA so bound bind the live cells and penetrates the live cells thereby selectively targeting live cells at a site of interest with the cell-penetrating polypeptide.

DETAILED DESCRIPTION OF THE INVENTION

Figure 1:
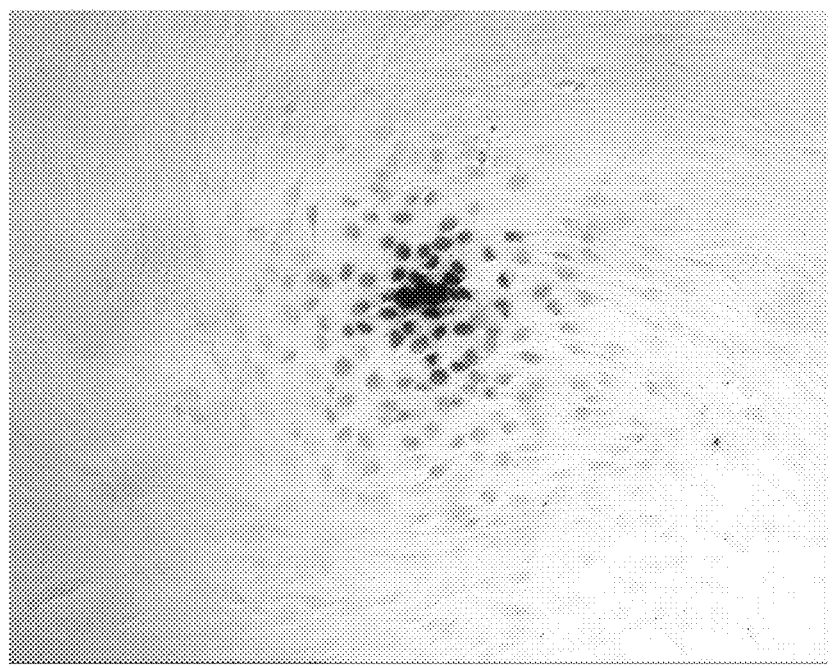
FIG. 1. 3E10 scFv penetrates most efficiently into living cells surrounding a dead cell. GM02605 fibroblasts were washed with serum free media and then treated with 10 µM 3E10 scFv for one hour, followed by anti-Myc immunostaining to detect nuclear penetration by 3E10 scFv. Nuclear penetration by 3E10 scFv was restricted to cells in close proximity to a dead cell, suggesting that a factor released by dead cells promotes nuclear uptake of the fragment.

It is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

The detailed description of the present disclosure is divided into various sections only for the reader's convenience and disclosure found in any section may be combined with that in another section. Unless defined otherwise, all technical and scientific terms used herein have the same meaning as commonly understood by one of ordinary skill in the art to which the present disclosure belongs.

Definitions

It must be noted that as used herein and in the appended claims, the singular forms "a", "an", and "the" include plural referents unless the context clearly dictates otherwise. Thus, for example, reference to "a compound" includes a plurality of compounds.

Unless defined otherwise, all technical and scientific terms used herein have the same meaning as commonly understood by one of ordinary skill in the art to which the present disclosure belongs. As used herein the following terms have the following meanings.

As used herein, the term "about" when used before a numerical designation, e.g., temperature, time, amount, concentration, and such other, including a range, indicates approximations which may vary by (+) or (−) 10%, 5% or 1%.

As used herein, the term "administration" may be effected in one dose, continuously or intermittently or by several subdoses which in the aggregate provide for a single dose. Dosing can be conducted throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include intratumoral delivery, peritumoral delivery, intraperitoneal delivery, intrathecal delivery, intramuscular injection, subcutaneous injection, intravenous delivery, nasal spray and other mucosal delivery (e.g. transmucosal delivery), intra-arterial delivery, intraventricular delivery, intrasternal delivery, intracranial delivery, intradermal injection, electroincorporation (e.g., with electroporation), ultrasound, jet injector, oral and topical patches.

A "therapeutic agent," as used herein, may be a molecule, or compound that is useful in treatment of a disease or condition. A "therapeutically effective amount," "therapeutically effective concentration" or "therapeutically effective dose" is the amount of a compound that produces a desired therapeutic effect in a subject, such as preventing or treating a target condition, alleviating symptoms associated with the condition, producing a desired physiological effect, or allowing imaging or diagnosis of a condition that leads to treatment of the disease or condition. The precise therapeutically effective amount is the amount of the composition that will yield the most effective results in terms of efficacy of treatment in a given subject. This amount will vary depending upon a variety of factors, including, but not limited to, the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy $21^{(st)}$ Edition, Univ. of Sciences in Philadelphia (USIP), Lippincott Williams & Wilkins, Philadelphia, Pa., 2005.

As used herein, "in combination" or "in combination with," when used herein in the context of multiple agents, therapeutics, or treatments, means in the course of treating the same disease or condition in a subject administering two or more agents, drugs, treatment regimens, treatment modalities or a combination thereof. This includes simultaneous administration (or "coadministration"), administration of a first agent prior to or after administration of a second agent, as well as in a temporally spaced order of up to several days apart. Such combination treatment may also include more than a single administration of any one or more of the agents, drugs, treatment regimens or treatment modalities. Further, the administration of the two or more agents, drugs, treatment regimens, treatment modalities or a combination thereof may be by the same or different routes of administration.

"Treating" or "treatment" of a condition, disease or disorder may refer to preventing the condition, disease or disorder, slowing the onset or rate of development of the condition, disease or disorder, reducing the risk of developing the condition, disease or disorder, preventing or delaying the development of symptoms associated with the condition, disease or disorder, reducing or ending symptoms associated with the condition, disease or disorder, generating a complete or partial regression of the condition, disease or disorder, or some combination thereof. Examples of diseases or disorders include colorectal cancer, osteosarcoma, non-small cell lung cancer, breast cancer, ovarian cancer, glial cancer, solid tumors, metastatic tumor, acute lymphoblastic leukemia, acute myelogenous leukemia, adrenocortical carcinoma, Kaposi sarcoma, lymphoma, anal cancer, astrocytomas, basal cell carcinoma, bile duct cancer, bladder cancer, bone cancer, brain tumor, breast cancer, bronchial tumor, cervical cancer, chronic lymphocytic leukemia, chronic myelogenous leukemia, chronic myeloproliferative disorders, colon cancer, colorectal cancers, ductal carcinoma in situ, endometrial cancer, esophageal cancer, eye cancer, intraocular, retinoblastoma, metastatic melanoma, gallbladder cancer, gastric cancer, gastrointestinal carcinoid tumor, gastrointestinal stromal tumors, glioblastoma, glioma, hairy cell leukemia, head and neck cancer, hepatocellular carcinoma, hepatoma, Hodgkin lymphoma, hypopharyngeal cancer, Langerhans cell histiocytosis, laryngeal cancer, lip and oral cavity cancer, liver cancer, lobular carcinoma in situ, lung cancer, non-small cell lung cancer, small cell lung cancer, lymphoma, AIDS-related lymphoma, Burkitt lymphoma, non-Hodgkin lymphoma, cutaneous T-cell lymphoma, melanoma, squamous neck cancer, mouth cancer, multiple myeloma, myelodysplastic syndromes, myelodysplastic/myeloproliferative neoplasms, nasal cavity and paranasal sinus cancer, nasopharyngeal cancer, neuroblastoma, oral cavity cancer, oropharyngeal cancer, osteosarcoma, ovarian cancer, pancreatic carcinoma, papillary carcinomas, parathyroid cancer, penile cancer, pharyngeal cancer, pheochromocytoma, pineal parenchymal tumors, pineoblastoma, pituitary tumor, pleuropulmonary blastoma, primary central nervous system lymphoma, prostate cancer, rectal cancer, renal cell cancer, salivary gland cancer, sarcoma, Ewing sarcoma, soft tissue sarcoma, squamous cell carcinoma, Sezary syndrome, skin cancer, Merkel cell carcinoma, testicular cancer, throat cancer, thymoma, thymic carcinoma, thyroid cancer, urethral cancer, endometrial cancer, uterine cancer, uterine sarcoma, vaginal cancer, vulvar cancer, Waldenstrom macroglobulinemia, and Wilms tumor.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein. Tumor or cancer status may also be assessed by sampling for the number, concentration or density of tumor or cancer cells, alone or with respect to a reference. In accordance with the practice of the invention, inhibiting a tumor may be measured in any way as is known and accepted in the art, including complete regression of the tumor(s) (complete response); reduction in size or volume of the tumor(s) or even a slowing in a previously observed growth of a tumor(s), e.g., at least about a 10-30% decrease in the sum of the longest diameter (LD) of a tumor, taking as reference the baseline sum LD (partial response); mixed response (regression or stabilization of some tumors but not others); or no apparent growth or progression of tumor(s) or neither sufficient shrinkage to qualify for partial response nor sufficient increase to qualify for progressive disease, taking as reference the smallest sum LD since the treatment started (stable disease).

Examples of cytotoxic agents include, but are not limited to ricin, ricin A-chain, doxorubicin, daunorubicin, taxol, ethidium bromide, mitomycin, etoposide, tenoposide, vincristine, vinblastine, colchicine, dihydroxy anthracenedione, actinomycin D, diphtheria toxin, *Pseudomonas* exotoxin (PE) A, PE40, abrin, abrin A chain, modeccin A chain, alpha-sarcin, gelonin, mitogellin, restrictocin, phenomycin, enomycin, curcin, crotin, calicheamicin, *saponaria officinalis* inhibitor, maytansinoids, and glucocorticoid and other chemotherapeutic agents, as well as radioisotopes such as $^{212}$Bi, $^{131}$I, $^{131}$In, $^{90}$Y and $^{186}$Re. Suitable detectable markers include, but are not limited to, a radioisotope, a fluorescent compound, a bioluminescent compound, chemiluminescent compound, a metal chelator or an enzyme.

An "isolated" antibody is one which has been identified and separated and/or recovered from a component of its natural environment or man-made environment in which the antibody is synthesized and/or assembled. An "isolated" antibody is deficient in and, preferably, eliminated of contaminant components of its natural environment or man-made environment in which the antibody is synthesized and/or assembled. Contaminant components of its natural environment or man-made environment are materials which would interfere with diagnostic or therapeutic uses for the antibody, and may include enzymes, hormones, and other proteinaceous or nonproteinaceous solutes. "Isolated" antibody does not require absolute purity. In some embodiments, the antibody will be purified (1) to greater than 95% by weight of antibody as determined by the Lowry method, and most preferably more than 99% by weight, or (2) to homogeneity by SDS-PAGE under reducing or nonreducing conditions using Coomassie blue or, preferably, silver stain. Other purification methods are well known and contemplated herein.

The term "vector," is intended to refer to a nucleic acid molecule capable of transporting another nucleic acid to which it has been linked. Examples of vectors include, but are not limited to, plasmids, (e.g., a circular double stranded DNA loop into which additional DNA segments may be ligated or introduced), phage vectors, and viral vectors (e.g., wherein additional DNA segments may be ligated or introduced into the viral genome). Certain vectors are capable of directing the expression of genes to which they are operatively linked. Such vectors are referred to herein as "recombinant expression vectors" (or simply, "recombinant vectors").

"Polynucleotide," or "nucleic acid," as used interchangeably herein, refer to polymers of nucleotides of any length, and include DNA and RNA. The nucleotides can be deoxyribonucleotides, ribonucleotides, modified nucleotides, and/or their analogs, or any substrate that can be incorporated into a polymer by DNA or RNA polymerase, or by a synthetic reaction.

The terms "antibody" and "immunoglobulin" are used interchangeably in the broadest sense and include monoclonal antibodies (for example, full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

The term "variable region" or "variable domain" refers to a region or domain, which is characterized by the presence of certain portions of the antibody differing extensively in sequence among antibodies and is used in the binding of each particular antibody to a particular antigen. The "variable region" or "variable domain" confers binding specificity to the antibody. Sequence variability is not evenly distributed throughout the variable domain or variable region of an antibody. Rather, sequence variability is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain may be covalently linked by a flexible peptide linker such that the light and heavy chains can associate in a "dimeric" structure analogous to that in a two-chain Fv species.

The Fab fragment contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. F(ab')$_2$ antibody fragments originally were produced as pairs of Fab' fragments which have hinge cysteines between them. Other chemical couplings of antibody fragments are also known.

"Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')$_2$, and Fv fragments; diabodies; linear antibodies; single-chain antibody molecules; single chain Fv fragment (scFv) and multispecific antibodies formed from antibody fragments. In one embodiment, an antibody fragment comprises an antigen binding site of the intact antibody and thus retains the ability to bind antigen. In another embodiment, an antibody fragment, for example, comprises the Fc region, retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise on antigen binding arm linked to an Fc sequence capable of conferring in vivo stability to the fragment.

"Framework" or "FR" residues are those variable domain residues other than the hypervariable region residues.

"Humanized" forms of non-human (e.g., murine) antibodies are chimeric antibodies that contain minimal sequence derived from non-human immunoglobulin. Humanized antibodies may be human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. The humanized antibody may optionally also comprise at least a portion of an immunoglobulin constant region (Fc), e.g. that of a human immunoglobulin.

"Chimeric" antibodies have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Morrison et al., Proc. Natl. Acad. Sci. USA 81:6851-6855 (1984)).

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For example, one embodiment of 3E10 mAb is a 3E10 scFv having the primary structure shown in FIG. 4-1 through 4-4 of U.S. Patent Application Publication No.: US 2013/0266570 A1, published 10 Oct. 2013.

An "antigen" is a target to which an antibody can selectively bind. The target antigen may be polypeptide, carbohydrate, nucleic acid, lipid, hapten or other naturally occurring or synthetic compound.

In accordance with the practice of the invention, "extracellular DNA" is DNA free of a cell or cell-free DNA. Extracellular DNA may be introduced or administered by methods known in the art such as, for example, microinjection of DNA into extracellular space or outside of a cell or cells, cell or cells in a tissue, or cell or cells in an organ, so long as the DNA is not introduced or administered into a cell. The delivered DNA in the extracellular space or outside of a cell may be in any physical state, including in a solution, as a solid, as a colloidal form, as a semi-crystalline state, as a nanoparticle or combination thereof. The delivered DNA may be isolated DNA from nature, either total, fractionated, intact or sheared, or synthesized by the hand of man such as through synthetic chemistry or in vitro enzymatic methods as known in the art. Alternatively, the extracellular DNA may be produced in situ by dying cells that release its nucleic acid content. In one embodiment, extracellular DNA is produced by radiation, chemotherapeutic agent, toxin, or by any condition that promotes cell death. In one embodiment, the invention contemplates the use of radiation or a chemotherapeutic agent at a site of interest or a site of injury to produce extracellular DNA or additional extracellular DNA. In another embodiment, extracellular DNA may be produced in situ through freezing, heat, laser, hypoxic condition, a poison, laceration, force and trauma.

A "bispecific antibody" of the invention includes antibodies with not only binding specificities for two targets but also include antibodies with additional determinants, which may be derived from immunoglobulin sequences or non-immunoglobulin sequences, with specificities for other target(s). For example, a bispecific antibody includes heteroconjugates with binding specificities for at least two different targets. For example a heteroconjugates includes a hybrid antibody created from linking two different antibodies or antibody fragments or a hybrid of an antibody or antibody fragment linked to a lectin or lectin fragment or another determinant with an intracellular binding specificity or a cell-penetrating ability, so long as the heteroconjugates have binding specificities for at least two targets. A bispecific antibody may further include heteroconjugates in which a bispecific antibody is coupled to a therapeutic agent (e.g., chemotherapeutic agent or toxin or cytoprotective agent) or an imaging agent (e.g., radioisotope). A bispecific antibody may be produced by recombinant DNA methods in which coding sequences of immunoglobulin genes are manipulated to produce the bispecific antibody. The coding sequences of the immunoglobulin genes may be used in its entirety, mutated at specific sequences or codons, or used partially by truncating the coding sequences to produce the bispecific antibody or components that results in production of a bispecific antibody. In some embodiments, a bispecific antibody includes an intact antibody or a Fv fragment, Fab, Fab' or F(ab')$_2$ fragment or a diabody, linear antibody, single-chain antibody molecule or scFv antibody fragment coupled chemically or recombinantly, disulfide bridges or by other means to a second determinant which specifically recognizes at least a different target than the target recognized by the intact antibody or the Fv, Fab, Fab' or F(ab')$_2$ fragment or the diabody, linear antibody, single-chain antibody molecule or scFv antibody fragment. The second determinant includes a second intact antibody or a Fv fragment, Fab, Fab' or F(ab')$_2$ fragment or a diabody, linear antibody, single-chain antibody molecule or scFv antibody fragment different from the binding specificity of the first antibody or the first Fv, Fab, Fab' or F(ab')$_2$ fragment or a the first diabody, linear antibody, single-chain antibody molecule or scFv antibody fragment.

In accordance with the practice of the invention, the second determinant may recognize a target that is located inside the cell, e.g., in the cytoplasm or in the cell nucleus. In another embodiment, the second determinant recognizes a target that is normally an intracellular protein and not normally on the surface of a cell or not normally secreted by the cell. In a further embodiment, the second determinant recognizes an E3 ubiquitin-protein ligase, a tumor suppressor-interacting protein, a binding partner of a tumor suppressor protein, an oncoprotein, or a DNA repair protein, wherein the second determinant fails to recognize any protein that normally resides on the cell surface. In yet a further embodiment, the second determinant recognizes a transcription factor, a transcriptional repressor, a transcriptional co-factor, a nuclear receptor, a steroid receptor, a methylase, an acetylase, a deacetylase, RNA polymerase, a kinase, a phosphatase, an intracellular signaling molecule (not a cell surface signaling molecule), a cell cycle regulatory protein, a protease, a DNA repair protein, a recombinase, a chromosomal protein, an apoptotic protein, a SUMO ligase, a ubiquitin ligase, a metabolic protein, an organelle protein, a nuclear protein, a nucleolar protein, a mitochondrial protein, a ligand, a ribosomal protein, an enzyme, a cytoskeletal protein, a chromosomal protein, a structural protein, a intracellular soluble protein, an intracellular shuttling protein or a regulatory protein so long as the second determinant fails to recognize any protein that normally resides on the cell surface.

A bispecific antibody includes chimeric antibodies, recombinant antibodies, humanized antibodies or human antibodies or their derivatives. A bispecific antibody includes antibodies of the invention in which one or more of the complementarity determining region (CDR) of the invention is used to screen for additional antibodies or agents that can compete with the binding of the 3E10 antibody. Peptide, phage display, cDNA, or chemical libraries may be used for such a screen.

Figure 2:
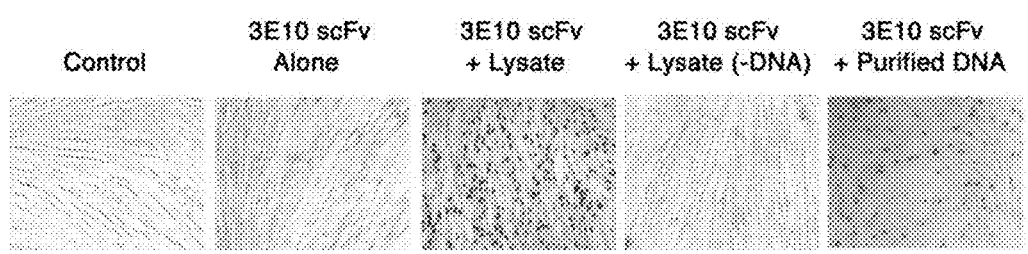
FIG. 2. Extracellular DNA facilitates penetration of 3E10 scFv into cell nuclei. GM02605 fibroblasts were washed with serum free media and then treated with control buffer alone or 10 µM 3E10 scFv in the presence of control buffer, cell lysate, DNA-depleted cell lysate, or purified DNA for one hour, followed by anti-Myc immunostaining to detect nuclear penetration by 3E10 scFv. Nuclear penetration into ~100% of the cells was only observed in the presence of cell lysate or purified DNA.
Figure 3:
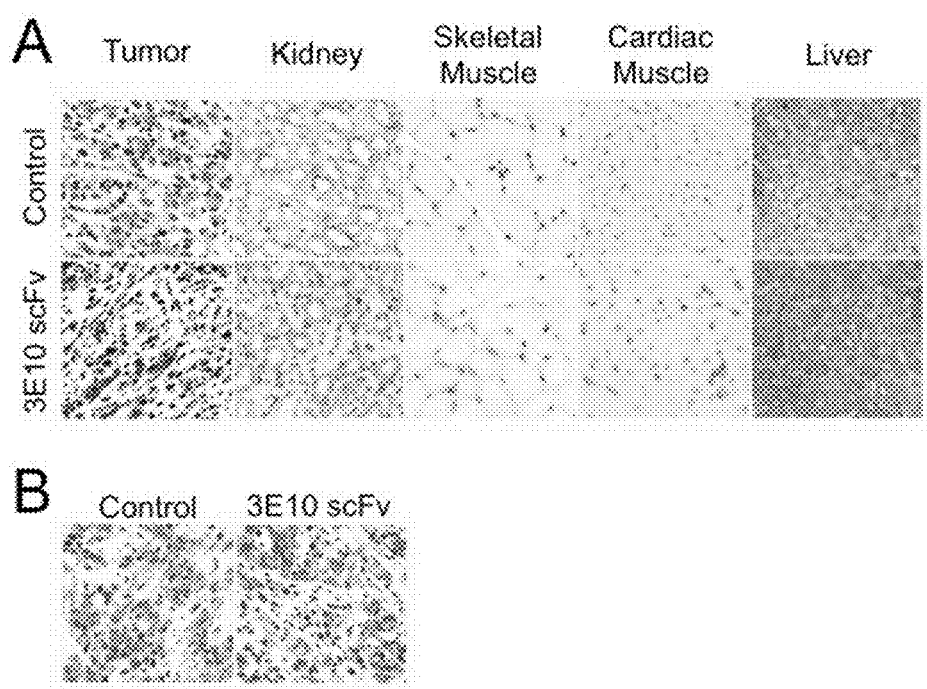
FIG. 3. 3E10 scFv localizes to tumor cell nuclei in vivo. Immunodeficient mice bearing subcutaneous U87 human glioma xenografts were treated by intraperitoneal injection of control buffer or 3E10 scFv. Mice were sacrificed 4 or 24 hours after treatment, and tumors and select normal tissues were immunostained for the presence of 3E10 scFv. (A) Four hours after treatment 3E10 scFv was detected in the nuclei of the U87 tumor cells but was not detected in tissues of major organs including heart, kidney, skeletal muscle, and liver. These results are consistent with enhanced uptake of 3E10 scFv into sites of high cell turnover where DNA is released from dying cells. (B) Twenty-four hours after treatment 3E10 scFv was still detectable in the tumors, demonstrating the stability of the uptake into tumor nuclei.

Examples of 3E10 bispecific antibodies, e.g., 3E10 scFv-3G5 scFv bispecific antibody and 3E10 scFv-PAb421 scFv bispecific antibody, are disclosed in U.S. Ser. No. 13/844,318, filed Mar. 15, 2013, which is incorporated by reference herein. Additional examples of anti-DNA monoclonal antibody 3E10 (also referred to herein as a 3E10 antibody or mAb 3E10) include an antibody produced by ATCC PTA 2439 or a functional fragment or variant thereof or an antibody having the specificity of mAb 3E10 (Chan G, et al., Int. J. Cancer 2016 138(1):182-6; Weisbart R H, et al., Sci. Rep. 2015 5:12022; Noble P W, et al., Cancer Res. 2015 75(11):2285-91; Hansen J E, et al., Sci. Transl. Med. 2012 24; 4(157):157ra142; Weisbart R H, et al., Mol. Cancer Ther. 2012 11(10):2169-73; Heinze E, et al., Oncol. Lett. 2011 2(4):665-668; Zhan X, et al., Stroke. 2010 41(3):538-43; Hansen J E, et al., J. Biol. Chem. 2007 282(29):20790-3; Hansen J E, et al., Cancer Res. 2007 67(4):1769-74; Hansen J E, et al., Brain Res. 2006 1088(1):187-96; Hansen J E, et al., Scientific World Journal. 2005 5:782-8; Weisbart R H, et al., J. Drug Target. 2005 13(2):81-7; Weisbart R H, et al., Int. J. Oncol. 2004 25(6):1867-73; Weisbart R H, et al., Int. J. Oncol. 2004 25(4):1113-8; Weisbart R H, et al., Cancer Lett. 2003 195(2):211-9; Weisbart R H, et al., Mol. Immunol. 2003 39(13):783-9; Weisbart R H, et al., J. Immunol. 2000 164(11):6020-6; Spertini F, et al., J Rheumatol. 1999 26(12): 2602-8; Weisbart R H, et al., J. Autoimmun. 1998 11(5): 539-46; Zack D J, et al., J. Immunol. 1996 157(5):2082-8; Zack D J, et al., Mol. Immunol. 1995 32(17-18):1345-53; Zack D J, et al., J. Immunol. 1995 154(4):1987-94; Zack D J, et al., Immunol. Cell Biol. 1994 72(6):513-20; and Weisbart R H, et al., J. Immunol. 1990 144(7):2653-8). The full 3E10 antibody has been previously described (Weisbart R H, et al., J. Immunol. 1990 144(7): 2653-2658; ATCC Accession No. PTA 2439 hybridoma; SEQ ID NOS.: 2 and 4 of PCT International Publication No.: WO 2010/148010 A1, published 23 Dec. 2010) as well as its nucleic acid sequence and protein sequence (FIGS. 3 and 4 of Zack D J, et al., J. Immunol. 1995 154(4): 1987-1994; FIGS. 3 and 4 of US Patent Application Publication No.: US 2008/0292618 A1; FIGS. 1 and 2 of PCT International Publication No.: WO 2010/138769 A1, published 2 Dec. 2010; GenBank Accession Numbers: L16982 for mAb 3E10 VH chain and L34051 for mAb 3E10 Vκ light chain). Location of the complement-determining regions (e.g., CDR1, CDR2 and CDR3) along with the framework regions (i.e., FR1, FR2, FR3, and FR4) of the 3E10 variable heavy chain and light chain domains are provided in FIGS. 3 and 4 of Zack D J, et al., J. Immunol. 1995 154(4): 1987-1994; FIGS. 3 and 4 of US Patent Application Publication No.: US 2008/0292618 A1; FIGS. 1 and 2 of PCT International Publication No. WO 2010/138769 A1, published 2 Dec. 2010. Particularly useful variant is substitution of aspartic acid (D) at amino acid position 31 of the heavy chain variable region (VH) of 3E10 antibody with asparagine (N), the D31N variant, which increases binding to ssDNA and dsDNA (Zack D J, et al., J. Immunol. 1995 154(4): 1987-1994) and enhances cell and nuclear penetration (Zack D J, et al., J. Immunol. 1996 157(5): 2082-2088; Weisbart W H, et al., J. Autoimmunity 11(5): 539-546). A preferred embodiment of 3E10 antibody or its fragment is 3E10 antibody or its fragment or derivative with aspartic acid to asparagine change at amino acid 31 of the VH chain, the D31N variant.

A "subject" is a vertebrate, preferably a mammal, more preferably a human. Mammals include, but are not limited to, farm animals (such as cows), pets (such as cats, dogs and horses), primates, mice and rats.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes, chemotherapeutic agents e.g. methotrexate, adriamycin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

According to the present invention, where administration includes a pharmaceutical formulation, preferably the formulation is a unit dosage containing a daily dose or unit, daily sub-dose or an appropriate fraction thereof, of the active ingredient (also referred to herein as a therapeutic agent). In one embodiment, the active ingredient comprises a cell-penetrating polypeptide of the invention. In one embodiment, the active ingredient comprises a cell-penetrating polypeptide-conjugate, such as a cell-penetrating polypeptide chemically crosslinked to a chemical, peptide or protein with a desired biological activity, a cell-penetrating polypeptide modified with a radioisotope or modified with a chelator bound to a radioisotope, or a cell-penetrating polypeptide linked to a peptide or protein (and produced) through recombinant DNA methods. In another embodiment, the active ingredient comprises a fusion protein of a cell-penetrating polypeptide and a second protein or peptide with a desired biological activity. In one embodiment, the desired biological activity may be an activity that induces cell death or is cell protective. In one embodiment, the active ingredient is DNA and/or its degradation product(s). In one embodiment, the active ingredient is extracellular DNA and/or its degradation product(s).

The compositions of the invention can be administered by any parenteral route, in the form of a pharmaceutical formulation comprising the active ingredient, optionally in the form of a nontoxic organic, or inorganic, acid, or base, addition salt, in a pharmaceutically acceptable dosage form. Depending upon the disorder and patient to be treated, as well as the route of administration, the compositions may be administered at varying doses.

In human therapy, compositions of the invention may be administered alone but may generally be administered in admixture with a suitable pharmaceutical excipient diluent or carrier selected with regard to the intended route of administration and standard pharmaceutical practice.

In embodiments of the present invention in which polypeptides or polynucleotides of the invention are administered parenterally, such administration can be, for example, intravenously, intra-arterially, intraperitoneally, intrathecally, intraventricularly, intracisternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Methods of the Invention

The invention is directed to the discovery that certain anti-DNA antibodies, including but not limited to, 3E10 monoclonal antibody or other anti-DNA antibodies that by their dependence on a salvage pathway for cell and nuclear penetration, require extracellular DNA or its degradation product in order to penetrate cells in a salvage pathway-dependent process, such as a nucleoside salvage pathway or ENT-2 nucleoside transporter pathway. This requirement for extracellular DNA or its degradation product for cell and nuclear penetration provides an opportunity for "targeted" therapies with these anti-DNA antibodies by introducing or producing extracellular DNA or its degradation product near or around live cells at a site of interest being targeted by these cell-penetrating anti-DNA antibodies. "Targeted" therapies, using such anti-DNA antibodies or their conjugates, reduce any potential systemic toxicity as well as increase effectiveness of the antibodies and their conjugates.

In one embodiment, the invention provides a method for selective targeting of live cells at a site of interest with a cell-penetrating polypeptide which comprises: (a) introducing or producing extracellular DNA and/or its degradation product(s) near or around the live cells at the site of interest; (b) introducing the cell-penetrating polypeptide comprising cell-penetrating determinants near or around the live cells, before, after or concurrently with the DNA of step (a); (c) contacting extracellular DNA or its degradation product near or around the live cells with a cell-penetrating polypeptide comprising cell-penetrating determinants so that the cell-penetrating polypeptide binds extracellular DNA or its degradation product near or around the live cells so as to form a complex; (d) contacting one of the live cells with the complex in (c) so as to bind and penetrate the live cell; and (e) permitting additional complexes to form as in (c) and contacting additional cells with said complexes so as to bind and penetrate additional live cells at the site of interest; thereby selectively targeting live cells at the site of interest with a cell-penetrating polypeptide.

In an embodiment of the invention, the extracellular DNA and/or its degradation product(s) is introduced or produced near or around the live cells at about less than 20 mm from the cells at the site of interest; less than 10 mm from cells at the site of interest; a range of between 0.5 mm to 5 mm from the cells at the site of interest; a range of between 0.5 mm to 20 mm from the cells at the site of interest; range of between 0.5 mm to 0.1 mm from the cells at the site of interest; range of less than 0.1 mm from the cells at the site of interest; range of between 100 µm to 10 µm from the cells at the site of interest; or directly into the site of interest (e.g., directly into the tumor mass or cancer). In another embodiment, the extracellular DNA and/or its degradation product(s) is introduced near or around the live cells in close proximity to a target cell, tissue or injury.

The invention provides methods for selective targeting of live cells, which have undergone or are undergoing radiation or chemotherapy, at a site of interest with a cell-penetrating polypeptide. In one embodiment of the invention, the method comprises contacting the live cells with a cell-penetrating polypeptide comprising cell-penetrating determinants so that the cell-penetrating polypeptide binds extracellular DNA near or around the live cells so as to form a complex or association therewith such that the complex or associated polypeptide-DNA so bound binds the live cells and penetrates the live cells thereby selectively targeting live cells at a site of interest with a cell-penetrating polypeptide. Examples of cell-penetrating polypeptides include cell-penetrating antibodies such as 3E10, 5C5, 5C6 and 4H2 (Weisbart R H, et al., J. Immunol. 1990 144(7): 2653-2658; Zack D J, et al., *J. Immunol.* 1995 154(4): 1987-1994; Weidle U H, et al., Cancer Genomics Proteomics 2013 10: 239-250; Weisbart R H, et al., Sci. Rep. 2015 5: 12022; Noble P W, et al., Sci. Rep. 2014 4:5958; Colburn K K, et al., J. Rheumatol. 2003 30(5):993-7). Examples of cell-penetrating determinants include, but are not limited to, cell-penetrating determinants from antibodies such as 3E10, 5C5, 5C6 and 4H2.

In one embodiment, the site of interest is an injury site. Examples of injury sites include but are not limited to an intracranial injury, brain injury, heart injury (e.g., myocardial infarction), skin injury, liver injury, gastrointestinal injury, lung injury, eye injury, kidney injury, pancreas injury, peritoneal injury, bone injury, nasopharyngeal injury, uterine injury, cervical injury, breast injury, organ injury, tissue injury, burn or radiation injury. An injury may include a cellular injury involving tissue or organ injury. Examples of cellular injury include any of chemical injury, excess reactive oxygen species, burn, hypothermia, ischemia, hypoxia, blunt force trauma, stress, heat shock, cold shock, hypothermia, mechanical stress, hypoxia, ischemia, cellular swelling, DNA damage, DNA fragmentation, membrane damage, organelle damage, damage due to heat, damage due to cold, damage due to radiation, damage due to chemical exposure, damage due to dehydration, mitochondrial damage, activation of apoptotic pathway, damage due to an infection, damage due to acidification, damage due to protein misfolding, damage due to intracellular protein aggregation, damage due to laser, damage due to aspiration, damage due to vacuum, damage due to cellular stress, injury due to damage to cell membrane, damage due to changes in osmotic pressure, or any cellular malfunction that results in cell death or results in altered cell proliferation that is deleterious, such as a cancer or other diseases or disorders referred to herein.

Additionally, the invention provides method for selective targeting of live cells at or near the proximity of a cellular injury with a cell-penetrating polypeptide which comprises cell-penetrating determinants which polypeptide is optionally joined to, or combined with, a therapeutic agent. In one embodiment, the method comprising administering the cell-penetrating polypeptide at or near the proximity of the injury so that it binds extracellular DNA from the cellular injury so as to form a complex or association therewith such that the complex or associated polypeptide-DNA-therapeutic agent so bound bind the live cells and penetrates the live cells thereby selectively targeting live cells at a site of interest with the cell-penetrating polypeptide.

In one embodiment, introducing the cell-penetrating polypeptide comprising cell-penetrating determinants before, after or concurrently with the DNA of step (a) is at a site other than near or around the live cells at the site of interest, such as the introduction of the cell-penetrating polypeptide via an intravenous injection to permit systemic circulation of the introduced cell-penetrating polypeptide.

The invention also provides methods for inhibiting cellular injury in a subject. In one embodiment the method comprises administering directly to the live cells at or near a site of cellular injury of the subject a cell-penetrating polypeptide comprising cell-penetrating determinants joined to a therapeutic agent. The method further comprises the step of contacting extracellular DNA or its degradation product with the cell-penetrating polypeptide so that the cell-penetrating polypeptide binds extracellular DNA or its degradation product near or around the live cells so as to form a complex. The live cell and the complex come in contact so that the complex can penetrate the live cell. Additional complexes are permitted to form and contact additional cells at the site of injury so that that the complexes penetrate additional live cells at the site of cellular injury; thereby, inhibiting cellular injury in the subject.

The invention also provides methods for inhibiting a cell or inducing cell death in a subject comprising administering directly to the live cells at or near a site of injury of the subject a cell-penetrating polypeptide comprising cell-penetrating determinants which polypeptide is optionally joined to a therapeutic agent. The method further comprises the step of contacting extracellular DNA or its degradation product near or around the live cells with the cell-penetrating polypeptide so that the cell-penetrating polypeptide binds extracellular DNA or its degradation product near or around the live cells thereby forming a complex which can bind and penetrate the live cell which induces cell death or inhibition. Additional complexes are permitted to form and contact additional cells at the site of injury so that that the complexes penetrate additional live cells live cells at the site of injury thereby inducing cell death or inhibition at or near a site of injury with the cell-penetrating polypeptide.

In one embodiment, "introducing or producing extracellular DNA and/or its degradation product(s) near or around the live cells at the site of interest" comprises administering DNA and/or its degradation product(s). In one embodiment, DNA is administered into the extracellular space or outside of a cell (e.g., not inside a cell) by any method known in the art, including injection, microinjection, microprojectile and implantation. In another embodiment, "introducing, producing or permitting presence of extracellular DNA and/or its degradation product(s) near or around the live cells at the site of interest" comprises a man-made intervention to produce localized cellular damage, such as through radiation (e.g., low dose radiation), chemotherapeutic agent, cytotoxic drug, toxin, hypoxia, blunt force trauma, hypothermia, burn or an infectious agent, so as to cause cell death and release of chromosomal DNA.

In one embodiment, the cell-penetrating polypeptide is administered or introduced at a site of interest. In another embodiment, the cell-penetrating polypeptide is administered or introduced (e.g., directly administered or introduced) near or around a site of interest. In an embodiment of the invention, a site of interest is a site of injury, e.g., cellular injury. In another embodiment, the cell penetrating polypeptide is administered or introduced at a site of cellular injury. In another embodiment, the cell-penetrating polypeptide is administered or introduced at a site away from the injury. Merely by way of example, the cell-penetrating polypeptide may be administered or introduced in a subject by subcutaneous injection, intramuscular injection or intravenous injection. In another example, the cell-penetrating polypeptide is administered or introduced to a subject wherein the cell-penetrating polypeptide circulates systemically.

In one embodiment, the extracellular DNA is administered or introduced at a site of interest. It may be coadministered with the cell-penetrating polypeptide. Alternatively, the extracellular DNA may be separately administered with the cell-penetrating polypeptide, e.g., administered before or after the administration of the cell-penetrating polypeptide. In one embodiment of the invention, the extracellular DNA is administered or introduced at a site of injury. In another embodiment, the extracellular DNA is administered or introduced at a site of cellular injury. In one embodiment, the extracellular DNA is administered or introduced (e.g., directly administered or introduced) near or around the live cells at a site of interest, e.g., a site of injury. In another embodiment, extracellular DNA is administered or introduced near or around the live cells at a site of cellular injury. In one embodiment, the extracellular DNA may be produced in situ through the use of cell damaging agents. In one embodiment, the extracellular DNA is produced by the act of man at a site of interest in a subject.

In another embodiment, the invention provides a method for inhibiting cellular injury in a subject comprising: (a) administering directly to the live cells at or near a site of cellular injury of the subject a cell-penetrating polypeptide comprising cell-penetrating determinants joined to a therapeutic agent; (b) contacting extracellular DNA or its degradation product with the cell-penetrating polypeptide so that the cell-penetrating polypeptide binds extracellular DNA or its degradation product near or around the live cells so as to form a complex; (c) contacting one of the live cells with the complex in (b) so as to bind and penetrate the live cell; and (d) permitting additional complexes to form as in (b) and contacting additional cells with said complexes so as to bind and penetrate additional live cells at the site of cellular injury; thereby, inhibiting cellular injury in the subject In a further embodiment, the invention provides a method for selective targeting of live cells at or near a site of cellular injury with a cell-penetrating polypeptide which comprises cell-penetrating determinants joined to a therapeutic agent, the method comprising: (a) contacting the live cells with a composition comprising (i) a cell-penetrating polypeptide which comprises cell-penetrating determinants joined to a therapeutic agent and (ii) extracellular DNA or its degradation product so that the cell-penetrating polypeptide binds extracellular DNA or its degradation product near or around the live cells so as to form a complex such that the complex so formed binds one of the live cells and penetrates the live cell; and (b) permitting additional complexes to form as in (a) and contacting additional cells with said complexes so as to bind and penetrate additional live cells at the site of cellular injury, thereby selectively targeting live cells at a site of cellular injury with a cell-penetrating polypeptide.

In yet a further embodiment, the invention provides a method for inducing cell death in a subject comprising: (a) administering directly to the live cells at or near a site of injury of the subject a cell-penetrating polypeptide comprising cell-penetrating determinants joined to a therapeutic agent; (b) contacting extracellular DNA or its degradation product near or around the live cells with the cell-penetrating polypeptide so that the cell-penetrating polypeptide binds extracellular DNA or its degradation product near or around the live cells so as to form a complex; (c) contacting one of the live cells with the complex in (b) so as to bind and penetrate the live cell which induces cell death; and (d) permitting additional complexes to form as in (b) and contacting additional cells with said complexes so as to bind and penetrate additional live cells inducing additional cell death at the site of injury; thereby inducing cell death at or near a site of injury with the cell-penetrating polypeptide.

In yet another embodiment, the methods of the invention further provides the step of administering DNA and/or its degradation product (s) to the injury site or to a site of interest in an extracellular space to facilitate further selective targeting. In one embodiment, the introduced or administered DNA is a double-stranded DNA. In another embodiment, the introduced or administered DNA is a single-stranded DNA. In one embodiment, the introduced or administered DNA is isolated or purified DNA isolated from a cell (e.g., DNA from a cell lysate or purified from a cell), a virus or a bacteriophage. In an embodiment of the invention, the introduced or administered DNA may have modified bases (e.g., 5-methyl-cytosine). In an embodiment of the invention, the introduced or administered DNA is synthesized DNA such as a chemically synthesized oligonucleotide with or without modified bases. In an embodiment of the invention, the DNA so introduced or administered is not purified away from non-DNA nucleic acid (e.g., RNA), nucleotide, nucleoside or purine or pyrimidine base. In an embodiment of the invention, the DNA so introduced or administered is purified away from non-DNA nucleic acid, nucleotide, nucleoside or purine or pyrimidine base.

In an embodiment of the invention, the administered DNA is a polymer of thymidine monophosphate (dTMP) or poly (dT). In a further embodiment, the administered DNA comprises a thymidine or dT or thymine-deoxyribose. For example, in one embodiment a 3E10 antibody or fragment thereof has a higher binding affinity to single stranded DNA comprising a dT in the DNA sequence. As a further example, the single stranded DNA so introduced or administered comprises a poly (dT) sequence.

The DNA may be single-stranded DNA having a length of about 40,000 bases to about 2 bases or dinucleotide. In a further embodiment, the DNA may have a length of about more than 1,000 bases. In another embodiment, the DNA may have a length of about more than 2000 bases. In yet another embodiment, the DNA may have a length of about less than 2000 bases. In another embodiment, the DNA may have a length of about 50 bases to 500 bases. In yet another embodiment, the DNA may have a length of about less than 100 bases.

The DNA may be double stranded DNA having a length of about less than 20 kilobase pairs (kb pairs) to about 5 bp. In one embodiment, the DNA may have a length of about less than 2000 base pair (bp). In one embodiment, the DNA may have a length of about more than 2000 base pair (bp). In another embodiment, the DNA may have a length of about 50 bp to 500 bp. In yet another embodiment, the DNA may have a length of about less than 100 bp. In one embodiment, the DNA is purified calf thymus double stranded DNA sheared to an average length of 2000 bp.

In one embodiment, the DNA is non-infectious DNA (e.g., complete viral genome) or enzymatic DNA (e.g., DNAzyme). Preferably, the DNA is non-infectious DNA.

In one embodiment, the DNA is partially degraded DNA in the DNA-antibody complex or DNA-cell-penetrating polypeptide complex before cell penetration by the antibody or cell-penetrating polypeptide.

In one embodiment, the DNA and/or its degradation product(s) may be single-stranded, double-stranded, triple-stranded, or four-stranded or a combination thereof.

In an embodiment of the invention, the dose of the DNA and/or its degradation product(s) so introduced or administered may be between about 100 µg to 1 µg, between about 1 µg to 100 ng DNA, between about 100 ng to 10 ng DNA, between about 10 ng to 1 ng DNA, between about 1 ng to 100 pg DNA, between about 100 pg to 10 pg DNA, or between 10 pg to 1 pg DNA. In one embodiment, the dose is less than 1 ng DNA. In yet a further embodiment, the dose may be may be less than about 100 pg DNA. Factors to be considered in choice of actual dose include condition and tissue/organ being treated, number of cells at the site of interest to be treated, size of the tumor, size of the injury or ischemia, diffusibility of DNA and/or its degradation product(s) from the site of interest, tumor, injury site or ischemic site, and volume of the extracellular space at and around the site of interest. Doses will need to be adjusted based on the desired outcome. Multiple doses may need to be introduced or administered.

In one embodiment, the dose of the DNA and/or its degradation product(s) is DNA. In another embodiment, the dose of the DNA and/or its degradation product(s) is its degradation product(s). In one embodiment, the DNA degradation product(s) may be directly obtained from degradation DNA. In another embodiment, the DNA degradation product(s) may be equivalent to the degradation product(s) directly produced from the DNA. In another embodiment, the DNA degradation product(s) nucleotide, nucleoside, pyrimidine base and/or purine base. In another embodiment, the DNA degradation product(s) is produced in situ from the introduced or administered DNA. In yet another embodiment, the dose of the DNA and/or its degradation product(s) is or comprises both DNA and its degradation product(s).

The DNA and/or its degradation product(s) introduced or administered may be in a liquid formulation or a solid formulation. In one embodiment of a liquid formulation, the liquid formulation comprises DNA and/or its degradation product(s) and an aqueous carrier, preferably isotonic, at a DNA and/or its degradation product(s) concentration of less than 20 mg/ml, a DNA and/or its degradation product(s) concentration between 10 mg/ml to 1 mg/ml, a DNA concentration between 1 mg/ml to 100 µg/ml, a DNA and/or its degradation product(s) concentration between 100 µg/ml to 10 µg/ml, a DNA and/or its degradation product(s) concentration between 10 µg/ml to 1 µg/ml, a DNA and/or its degradation product(s) concentration between 1 µg/ml to 100 ng/ml, a DNA and/or its degradation product(s) concentration between 100 ng/ml to 10 ng/ml, or a DNA and/or its degradation product(s) concentration between 10 ng/ml to 1 ng/ml. In one embodiment, the DNA and/or its degradation product(s) concentration is less than 1 µg/ml. In one embodiment, the DNA and/or its degradation product(s) concentration is greater than 1 µg/ml. In a solid formation, the DNA and/or its degradation product(s) may be in the form of free acid or preferably in a salt. In one embodiment, the solid formulation is an immediate-release formulation comprising DNA and/or its degradation product(s) and a suitable carrier. In one embodiment, the solid formulation is a sustained-release formulation comprising DNA and/or its degradation product(s) and a suitable carrier. In one embodiment, the solid formulation is a combination of an immediate-release formulation and sustained-release formulation.

In one embodiment, the liquid formulation comprises a cell-penetrating polypeptide and DNA and/or its degradation product(s). In one embodiment, the solid formulation comprises a cell-penetrating polypeptide and DNA and/or its degradation product(s). In a further embodiment, the cell-penetrating polypeptide and DNA is in a cell-penetrating polypeptide-DNA complex or association. In another embodiment, the cell-penetrating polypeptide and DNA degradation product(s) is in a cell-penetrating polypeptide-DNA degradation product complex or association.

For example, in one embodiment, a site of interest is an injury site that may be created through the use of a cell-damaging agent. Examples of cell-damaging agents include, but are not limited to, a radioisotope, cytotoxic agent or radiation. Suitable examples of radioisotope include $^{46}$Sc, $^{47}$Sc, $^{48}$Sc, $^{67}$Cu, $^{67}$Ga, $^{72}$Ga, $^{73}$Ga, $^{90}$Y, $^{67}$Cu, $^{109}$Pd, $^{111}$Ag, $^{111}$In, $^{125}$, $^{131}$I, $^{149}$Pm, $^{153}$Sm, $^{166}$Ho, $^{177}$Lu, $^{186}$Re, $^{188}$Re, $^{211}$At, $^{211}$Bi, $^{212}$Bi, $^{212}$Pb, $^{213}$Bi, $^{214}$Bi and $^{225}$Ac. Suitable cytotoxic agents include ricin, ricin A-chain, doxorubicin, daunorubicin, paclitaxel, taxol, ethidium bromide, mitomycin, etoposide, tenoposide, vincristine, vinblastine, colchicine, dihydroxy anthracenedione, actinomycin D, diphtheria toxin, *Pseudomonas* exotoxin (PE) A, PE40, abrin, abrin A chain, modeccin A chain, alpha-sarcin, gelonin, mitogellin, restrictocin, phenomycin, enomycin, curcin, crotin, calicheamicin, *saponaria officinalis* inhibitor, maytansinoids, and glucocorticoid. Examples of radiation include microwave, infrared, ultraviolet, X-ray, gamma ray, alpha particle radiation, beta ray and ionizing radiation.

In one embodiment, the injury site is created through the use of a cell-damaging agent wherein the cell-damaging agent is a DNA damaging agent. In one embodiment, the DNA damaging agent is doxorubicin. In one embodiment, the injury site is created through the use of a cell-damaging agent wherein the cell damaging agent is a DNA damaging agent other than doxorubicin. In one embodiment, the injury site is created through the use of a cell-damaging agent other than a DNA-damaging agent. In one embodiment, the injury site is created through the use of a cell-damaging agent other than a DNA-damaging agent is taxol.

In one embodiment, the injury site is created through the use of radiation. Examples of radiation include microwave, infrared, ultraviolet, X-ray, gamma ray, alpha particle radiation, beta ray and ionizing radiation. In one embodiment, the injury site is created through means other than through the use of radiation. Examples of radiation include microwave, infrared, ultraviolet, X-ray, gamma ray, alpha particle radiation, beta ray and ionizing radiation.

In one embodiment, the site of interest comprises extracellular DNA. In another embodiment, the site of interest is devoid or substantially devoid of extracellular DNA. In one embodiment, the site of interest is a site within an in vitro cell or organ culture. In one embodiment, the site of interest is an in vivo site. In one embodiment, the site of interest is a site within a subject or a mammal.

The invention further provides methods for selective targeting of live cells at or near the proximity of a cellular injury with a cell-penetrating polypeptide. In an embodiment of the invention, the cell-penetrating determinants are joined to, or combined with (e.g., as an admix), a therapeutic agent. The method may comprise contacting the live cells with a composition having (a) a cell-penetrating polypeptide which comprises cell-penetrating determinants and (b) extracellular DNA so that the cell-penetrating polypeptide binds extracellular DNA near or around the live cells so as to form a complex or association therewith such that the complex or associated polypeptide-DNA so bound bind the live cells and penetrate the live cells thereby selectively targeting live cells at a site of interest with the cell-penetrating polypeptide.

The invention also provides method for inhibiting a tumor associated with ischemia, cellular/tissue necrosis or cellular/tissue apoptosis by selective targeting of live cells at a site of interest by any of the methods of the invention.

Examples of tumors include colorectal cancer, osteosarcoma, non-small cell lung cancer, breast cancer, ovarian cancer, glial cancer, solid tumors, metastatic tumor, acute lymphoblastic leukemia, acute myelogenous leukemia, adrenocortical carcinoma, Kaposi sarcoma, lymphoma, anal cancer, astrocytomas, basal cell carcinoma, bile duct cancer, bladder cancer, bone cancer, brain tumor, breast cancer, bronchial tumor, cervical cancer, chronic lymphocytic leukemia, chronic myelogenous leukemia, chronic myeloproliferative disorders, colon cancer, colorectal cancers, ductal carcinoma in situ, endometrial cancer, esophageal cancer, eye cancer, intraocular, retinoblastoma, metastatic melanoma, gallbladder cancer, gastric cancer, gastrointestinal carcinoid tumor, gastrointestinal stromal tumors, glioblastoma, glioma, hairy cell leukemia, head and neck cancer, hepatocellular carcinoma, hepatoma, Hodgkin lymphoma, hypopharyngeal cancer, Langerhans cell histiocytosis, laryngeal cancer, lip and oral cavity cancer, liver cancer, lobular carcinoma in situ, lung cancer, non-small cell lung cancer, small cell lung cancer, lymphoma, AIDS-related lymphoma, Burkitt lymphoma, non-Hodgkin lymphoma, cutaneous T-cell lymphoma, melanoma, squamous neck cancer, mouth cancer, multiple myeloma, myelodysplastic syndromes, myelodysplastic/myeloproliferative neoplasms, nasal cavity and paranasal sinus cancer, nasopharyngeal cancer, neuroblastoma, oral cavity cancer, oropharyngeal cancer, osteosarcoma, ovarian cancer, pancreatic carcinoma, papillary carcinomas, parathyroid cancer, penile cancer, pharyngeal cancer, pheochromocytoma, pineal parenchymal tumors, pineoblastoma, pituitary tumor, pleuropulmonary blastoma, primary central nervous system lymphoma, prostate cancer, rectal cancer, renal cell cancer, salivary gland cancer, sarcoma, Ewing sarcoma, soft tissue sarcoma, squamous cell carcinoma, Sezary syndrome, skin cancer, Merkel cell carcinoma, testicular cancer, throat cancer, thymoma, thymic carcinoma, thyroid cancer, urethral cancer, endometrial cancer, uterine cancer, uterine sarcoma, vaginal cancer, vulvar cancer, Waldenstrom macroglobulinemia, and Wilms tumor. In one embodiment, the tumor is a glioma. In one embodiment, the tumor is a tumor other than a glioma.

In one embodiment, the tumor is associated with an amplification or over activity of an oncogene. In one embodiment, the tumor is associated with a loss or under activity of a tumor suppressor gene. In one embodiment, the tumor suppressor gene is BRCA2. In one embodiment, the tumor is associated with a loss or under activity of a tumor suppressor gene, other than BRCA2. In one embodiment, the tumor is associated with amplification or over activity of an oncogene and loss or under activity of a tumor suppressor gene. In one embodiment, the tumor is associated with a loss or mutation of a gene for a DNA repair enzyme. In one embodiment, the gene for a DNA repair enzyme is RAD51 or its homolog. In one embodiment, the tumor is free of a loss or mutation of a gene for a DNA repair enzyme. In one embodiment, the tumor is free of a mutation in the RAD51 gene or its homolog.

The invention provides methods for increasing uptake and enhancing efficacy of a cell-penetrating polypeptide comprising an anti-DNA antibody or a derivative or variant thereof in targeting tumor or cancer cells comprising (a) inducing additional extracellular DNA release at or near the tumor or cancer cells through the use of a cell-damaging agent or introducing additional extracellular DNA or artificial DNA at or near the tumor or cancer cells, (b) administering the cell-penetrating polypeptide, (c) allowing the cell-penetrating polypeptide to form additional complexes with the additional extracellular DNA or artificial DNA, and (d) permitting the additional complexes in (c) to contact the tumor or cancer cells, thereby increasing uptake and enhancing efficacy of a cell-penetrating polypeptide comprising an anti-DNA antibody or a derivative or variant thereof in targeting tumor or cancer cells.

Also, the invention provides methods for enhancing the effects of chemotherapy or radiation therapy by selectively targeting live cells by any of the methods of the invention.

In accordance with the practice of the invention, any of the methods of the invention may be an adjunct therapy to a chemotherapy or a radiation therapy. The chemotherapy or the radiation therapy may be administered concurrently or before selectively targeting the live cells by any of the methods of the invention.

The invention further provides method for protecting cells (cytoprotection) from a disease or disorder associated with a hydrogen peroxide toxicity or reactive oxygen species (ROS) toxicity by selective targeting of live cells at the injury site by any of the methods of the invention. The disease or disorder may be a brain injury, heart injury, skin injury, or radiation injury and may be an acute injury. Examples of brain injury include but are not limited to brain trauma, spinal cord injury, peripheral nerve injury, or stroke. A heart injury may include but not limited to a myocardial infarction. Examples of skin injury include but are not limited to wound, burn, or decubitus ulcer. A radiation injury may include but not limited to burn or poison. In another embodiment, the disease or disorder may be acute renal failure, acute organ failure, liver injury, bowel infarction, peripheral vascular disease, pulmonary failure, or a cancer.

The cell-penetrating polypeptide may be a therapeutic agent. In one embodiment, the therapeutic agent may be the anti-DNA antibody of the invention, e.g., 3E10 mAb or its fragment or its variant, free of any other pharmaceutically active agent. In another embodiment, the cell-penetrating polypeptide may comprise a therapeutic agent linked or coupled to an anti-DNA antibody of the invention. The therapeutic agent linked or coupled to an anti-DNA antibody of the invention may be a cytotoxic agent, a cytoprotective agent, or another antibody or its fragment with an intracellular-binding determinant. The intracellular-binding determinant may be to an oncoprotein, tumor suppressor gene, a transcription factor, a cell signaling molecule, a nuclear receptor, a steroid receptor, a cell signaling molecule, a protein kinase, a phosphatase, an acetylase, a ligase, a methylase, a protease, an enzyme, a shuttling protein, a nuclear protein, a nucleolar protein, transcription components, a soluble protein, a cytoskeletal protein and a membrane protein.

Additionally, the cell-penetrating polypeptide may be an anti-DNA antibody (e.g., polyclonal, monoclonal, chimeric, bispecific and humanized antibodies). In one embodiment, the anti-DNA antibody binds DNA (including single stranded or double stranded DNA). Examples of suitable anti-DNA antibodies include, but are not limited to, 3E10 antibody, H7 antibody, H9 antibody, H72 antibody, H205 antibody, H317 antibody F14-6 antibody, SN22 antibody, SN50 antibody, SN111 antibody, SN112 antibody, SN575 antibody, SN604 antibody, SN608 antibody, F4.1 antibody, J20.8 antibody, F14.6 antibody, and 9D7 antibody or a derivative or variant thereof (Vlahakos D, Foster M H, Ucci A A, Barrett K J, Datta S K, and Madaio M P (1992) "Murine monoclonal anti-DNA antibodies penetrate cells, bind to nuclei, and induce glomerular proliferation and proteinuria in vivo." *J. Am. Soc. Nephrol.* 2(8):1345-54; Ruiz-Argüelles A, Perez-Romano B, Llorente L, Alarcón-Segovia D, and Castellanos J M (1998) "Penetration of anti-DNA antibodies into immature live cells." *J. Autoimmun.* 11(5):547-56; Avrameas A, Ternynck T, Nato F, Buttin G, and Avrameas S (1998) "Polyreactive anti-DNA monoclonal antibodies and a derived peptide as vectors for the intracytoplasmic and intranuclear translocation of macromolecules" *Proc. Natl. Acad. Sci. U.S.A.* 95(10):5601-5606; Song Y C, Sun G H, Lee T P, Huang J C, Yu C L, Chen C H, Tang S J, and Sun K H (2008) "Arginines in the CDR of anti-dsDNA autoantibodies facilitate cell internalization via electrostatic interactions." *Eur. J. Immunol.* 38(11):3178-90). Sequence of CDR for F4.1 antibody, J20.8 antibody and F14.6 antibody may be found in Avrameas A, Ternynck T, Nato F, Buttin G, and Avrameas S (1998) "Polyreactive anti-DNA monoclonal antibodies and a derived peptide as vectors for the intracytoplasmic and intranuclear translocation of macromolecules" *Proc. Natl. Acad. Sci. U.S. A.* 95(10):5601-5606. Sequence of CDR for 9D7 antibody may be found in Song Y C, Sun G H, Lee T P, Huang J C, Yu C L, Chen C H, Tang S J, and Sun K H (2008) "Arginines in the CDR of anti-dsDNA autoantibodies facilitate cell internalization via electrostatic interactions." *Eur. J. Immunol.* 38(11):3178-90. In one embodiment, the anti-DNA antibody is an isolated monoclonal antibody or a derivative or variant thereof. In an embodiment, the isolated monoclonal antibody or a derivative or variant thereof is taken up by live cells in the presence of extracellular nucleic acid, DNA or artificial DNA. In an embodiment, the isolated monoclonal antibody or a derivative or variant thereof allows for targeted uptake of cells with an increased concentration of extracellular nucleic acid, DNA or artificial DNA. In an embodiment, the cells targeted for uptake of the isolated monoclonal antibody or a derivative or variant are diseased or tumor cells. In an embodiment, the isolated monoclonal antibody or a derivative or variant is targeted to a live cell or any cell within a group of live cells at a site within an animal or human by targeted delivery of a cytotoxic agent or radiation to induce limited cell death and subsequent release of DNA around or near the live cell or around, near or in a group of live cells. In one embodiment, the isolated monoclonal antibody or a derivative or variant is targeted to a live cell or any cell within a group of live cells at a site within an animal or human by targeted delivery of a nucleic acid, DNA or artificial DNA. In one embodiment, such targeted delivery of a nucleic acid, DNA or artificial DNA may be achieved by an implant or transplant of an object, substance, cells or cell-based material containing nucleic acid, DNA or artificial DNA. The implant or transplant may release nucleic acid, DNA or artificial DNA in a single burst or over an extended period. In a preferred embodiment, the anti-DNA antibody is an isolated monoclonal antibody 3E10 as produced by a hybridoma having ATCC accession number PTA 2439 or a derivative or variant thereof. In one embodiment, the variant has a change in the amino acid sequence of a 3E10 scFv, wherein the change in the amino acid sequence does not abolish or prevent cell penetration.

In one embodiment, the cell-penetrating polypeptide is a 3E10 bispecific antibody having an Fv fragment with the cell-penetrating determinant which is a 3E10 Fv and a second Fv fragment with an intracellular target-binding determinant which is a 3G5 Fv.

In another embodiment, the bispecific antibody comprises an Fv fragment with a cell-penetrating determinant of anti-DNA monoclonal antibody 3E10 and a second Fv fragment with an intracellular target-binding determinant for MDM2.

In one embodiment, the cell-penetrating polypeptide is a 3E10 bispecific antibody having an Fv fragment with the cell-penetrating determinant which is a 3E10 Fv and a second Fv fragment with an intracellular target-binding determinant which is a PAb421 Fv.

In another embodiment, the bispecific antibody comprises an Fv fragment with a cell-penetrating determinant of anti-DNA monoclonal antibody 3E10 and a second Fv fragment with an intracellular target-binding determinant for p53.

Examples of 3E10 bispecific antibodies, e.g. 3E10 scFv and 3G5 scFv as well 3E10 scFv and PAb421 scFv, are disclosed in U.S. Ser. No. 13/844,318, filed Mar. 15, 2013, which is incorporated by reference herein.

The 3E10 bispecific antibodies of the invention may further comprise one or more amino acid sequence comprising Ala-Gly-Ile-His (AGIH) at the amino terminus of one or both of the Fv regions. Cell-penetrating polypeptides may further comprise one or more amino acid sequence comprising Ala-Gly-Ile-His (AGIH) at the amino terminus.

In another embodiment, the cell-penetrating polypeptide comprises a 3E10 Fv attached to a heat shock protein (Hsp). Examples of heat shock proteins include but are not limited to, human Hsp-70 (Hunt and Morimoto PNAS Vol, 82, pp. 64-55-6459, FIGS. 2 and 3); HspA (e.g., HspA1A, HspA1B, HspA1L, HspA2, HspA5, HspA6, HspA7, HspA8, HspA9, HspA12A, HspA12B, HspA13, HspA14); HspH (e.g., HspH1, HspH2, HspH3, and HspH4); Hsp40 (e.g., DnaJA (e.g. DNAJA1, DNAJA2, DNAJA3, and DNAJA4), DnaJB (e.g., DNAJB1, DNAJB2, DNAJB3, DNAJB4, DNAJB5, DNAJB6, DNAJB7, DNAJB8, DNAJB9, DNAJB11, DNAJB12, DNAJB13, and DNAJB14), DnaJC (e.g., DNAJC1, DNAJC2, DNAJC3, DNAJC4, DNAJC5B, DNAJC5G, DNAJC6, DNAJC7, DNAJC8, DNAJC9, DNAJC10, DNAJC11, DNAJC12, DNAJC13, DNAJC14, DNAJC15, DNAJC16, DNAJC17, DNAJC18, DNAJC19, DNAJC20, DNAJC21, DNAJC22, DNAJC23, DNAJC24, DNAJC25, DNAJC26, DNAJC27, DNAJC28, and DNAJC30) and HSPB (HSPB1, HSPB2, HSPB3, HSPB4, HSPB5, HSPB6, HSPB7, HSPB8, HSPB9, HSPB10 and HSPB11) (Kampinga et al., Cell Stress and Chaperones (2009) 14:105-111).

In a further embodiment, the cell-penetrating polypeptide is a fusion protein comprising a 3E10 Fv joined to a Hsp-70 or portion thereof, and optionally, the 3E10 Fv comprising an amino acid sequence AGIH at its amino terminus. Examples of 3E10 fusion proteins are disclosed in U.S. Ser. No. 13/815,829, filed Mar. 15, 2013, which is incorporated by reference herein.

In yet another embodiment, the cell-penetrating polypeptide is a fusion protein comprising a 3E10 Fv joined to Hsp-27 or portion thereof, and optionally, the 3E10 Fv comprising an amino acid sequence AGIH at its amino terminus.

The invention also provides a further embodiment, wherein the cell-penetrating polypeptide is a fusion protein comprising a 3E10 Fv attached or joined to a Hsp-90 or portion thereof, and optionally, the 3E10 Fv comprising an amino acid sequence AGIH at its amino terminus.

Additionally, the invention also provides an embodiment, wherein the cell-penetrating polypeptide is a fusion protein comprising a 3E10 Fv attached or joined to GRP78 or portion thereof, and optionally, the 3E10 Fv comprising an amino acid sequence AGIH at its amino terminus.

The invention also provides a further embodiment, wherein the cell-penetrating polypeptide is a fusion protein comprising a 3E10 Fv attached or joined to an E3 ubiquitin-protein ligase, a tumor suppressor-interacting protein, a binding partner of a tumor suppressor protein, an oncoprotein, or a DNA repair protein or portion thereof, and optionally, the 3E10 Fv comprising an amino acid sequence AGIH at its amino terminus. Fusion proteins may be produced by recombinant DNA methods in which coding sequences isolated from at least two different sources are assembled in a single nucleic acid molecule so as to allow the production of a single polypeptide for the fusion protein, also called chimeric protein.

The invention also provides a further embodiment, wherein the cell-penetrating polypeptide is a fusion protein comprising a 3E10 Fv attached or joined to a transcription factor, a transcriptional repressor, a transcriptional co-factor, a nuclear receptor, a steroid receptor, a methylase, an acetylase, a deacetylase, RNA polymerase, a kinase, a phosphatase, an intracellular signaling molecule (not a cell surface signaling molecule), a cell cycle regulatory protein, a protease, a DNA repair protein, a recombinase, a chromosomal protein, an apoptotic protein, a SUMO ligase, a ubiquitin ligase, a metabolic protein, an organelle protein, a nuclear protein, a nucleolar protein, a mitochondrial protein, a ligand, a ribosomal protein, an enzyme, a cytoskeletal protein, a chromosomal protein, a structural protein, a intracellular soluble protein, an intracellular shuttling protein or a regulatory protein or portion thereof, so long as the second determinant fails to recognize any protein that normally resides on the cell surface. In a further embodiment, the fusion protein comprises an amino acid sequence AGIH at its amino terminus.

In one embodiment, the cell-penetrating polypeptide is a fusion protein comprising a 3E10 Fv attached or joined to a nuclear transcription factor, or portion thereof, that is both a tumor suppressor factor and regulatory of T-regulatory cell. In one embodiment, the nuclear transcription factor that is both a tumor suppressor factor and regulatory of T-regulatory cell is Foxp3. In one embodiment, the cell-penetrating polypeptide is a fusion protein comprising a 3E10 Fv attached or joined to Foxp3 or portion thereof. In one embodiment, the cell-penetrating polypeptide is a fusion protein comprising a 3E10 Fv attached or joined to Foxp3 or portion thereof as described in Heinze E, et al., Oncol Lett. 2011 2(4): 665-668.

In one embodiment, the cell-penetrating polypeptide is a fusion protein comprising a 3E10 Fv attached or joined to a tumor suppressor or portion thereof. In one embodiment, the tumor suppressor factor is a p53 tumor suppressor protein. In one embodiment, the cell-penetrating polypeptide is a fusion protein comprising a 3E10 Fv attached or joined to p53 tumor suppressor or portion thereof. In one embodiment, the cell-penetrating polypeptide is a fusion protein comprising a 3E10 Fv attached or joined to p53 tumor suppressor or portion thereof as described in Weisbart R H, et al., Cancer Lett. 2003 195(2):211-9.

In yet a further embodiment, the cell-penetrating polypeptide is a 3E10 Fv attached to an Hsp-70 or portion thereof, the 3E10 Fv comprising an amino acid sequence AGIH at its amino terminus.

In an additional embodiment, the cell-penetrating polypeptide is a 3E10 Fv attached to Hsp-27 or portion thereof, the 3E10 Fv comprising an amino acid sequence AGIH at its amino terminus.

The invention also provides an embodiment, wherein the cell-penetrating polypeptide is a 3E10 Fv attached to a Hsp-90 or portion thereof, the 3E10 Fv comprising an amino acid sequence AGIH at its amino terminus.

In an additional embodiment, the cell-penetrating polypeptide is a 3E10 Fv attached to glucose regulated protein 78 kDa (GRP78) or portion thereof, the 3E10 Fv comprising an amino acid sequence AGIH at its amino terminus.

For example, chimeric antibodies of the invention may be immunoglobulin molecules that comprise a human and non-human portion. The antigen combining region (variable region) of a chimeric antibody can be derived from a non-human source (e.g. murine) and the constant region of the chimeric antibody which confers biological effector function to the immunoglobulin can be derived from a human source. The chimeric antibody should have the antigen binding specificity of the non-human antibody molecule and the effector function conferred by the human antibody molecule.

In general, the procedures used to produce chimeric antibodies can involve the following steps:
a) identifying and cloning the correct gene segment encoding the antigen binding portion of the antibody molecule; this gene segment (known as the VDJ, variable, diversity and joining regions for heavy chains or VJ, variable, joining regions for light chains or simply as the V or variable region) may be in either the cDNA or genomic form;
b) cloning the gene segments encoding the constant region or desired part thereof;
c) ligating the variable region with the constant region so that the complete chimeric antibody is encoded in a form that can be transcribed and translated;
d) ligating this construct into a vector containing a selectable marker and gene control regions such as promoters, enhancers and poly(A) addition signals;
e) amplifying this construct in bacteria;
f) introducing this DNA into eukaryotic cells (transfection) most often mammalian lymphocytes;
g) selecting for cells expressing the selectable marker;
h) screening for cells expressing the desired chimeric antibody; and
i) testing the antibody for appropriate binding specificity and effector functions.

A chimeric antibody may include a "humanized" antibody in which one or more of the complementary-determining region (CDR) from the variable region of a non-human antibody (such as a mouse monoclonal antibody) may be used to replace the corresponding CDR in a human antibody, such that the resulting chimeric antibody has the framework region of a human antibody and one or more CDR of a non-human antibody. The chimeric or humanized antibody may be produced by recombinant DNA methods and may be a whole antibody, an antibody fragment, a bi-specific antibody, a single chain Fv antibody or combinations thereof.

Antibodies of several distinct antigen binding specificities have been manipulated by these protocols to produce chimeric proteins [e.g. anti-TNP: Boulianne et al., Nature 312:643 (1984); and anti-tumor antigens: Sahagan et al., J. Immunol. 137:1066 (1986)]. Likewise, several different effector functions have been achieved by linking new sequences to those encoding the antigen binding region. Some of these include enzymes [Neuberger et al., Nature 312:604 (1984)], immunoglobulin constant regions from another species and constant regions of another immunoglobulin chain [Sharon et al., Nature 309:364 (1984); Tan et al., J. Immunol. 135:3565-3567 (1985)]. Additionally, procedures for modifying antibody molecules and for producing chimeric antibody molecules using homologous recombination to target gene modification have been described (Fell et al., Proc. Natl. Acad. Sci. USA 86:8507-8511 (1989)).

In accordance with the practice of the invention, the DNA (e.g., extracellular DNA) may be a single-stranded, double-stranded, triple-stranded, or four-stranded or a combination thereof. Further, the extracellular DNA may comprise a phosphodiester bond, a phosphorothioate bond or a methylphosphonate bond or a combination thereof. For example, the DNA (e.g., extracellular DNA) may comprise a 5'-to-3' linkage, an inverted 5'-to-5' linkage or an inverted 3'-to-3' linkage or a combination thereof. The DNA may be isolated from nature or synthesized in a laboratory.

In one embodiment, the degradation product of DNA may be bound by the anti-DNA antibody of the invention. DNA degradation products include lower molecular weight DNAs, which may be single-stranded, double-stranded, triple-stranded, or four-stranded or a combination thereof. Further, DNA degradation products include nucleotides, nucleosides and nucleobases. In one embodiment of the invention, the DNA degradation product includes a thymine base, thymidine or a thymidine monophosphate (dTMP). In one embodiment, the thymidine monophosphate may be a 3' dTMP, 5' dTMP or cyclic 3', 5' dTMP.

In one embodiment of the invention, the DNA degradation product comprises a guanine base, deoxyguanosine or a deoxyguanosine monophosphate (dGMP) or a combination thereof. In one embodiment, the dGMP may be a 3' dGMP, 5' dGMP or cyclic 3', 5' dGMP.

Further, in one embodiment of the invention, the DNA (e.g., extracellular DNA) comprises an artificial DNA. For example, the artificial DNA may comprise a DNA mimetic. In one embodiment, the DNA mimetic comprises a pseudopeptide backbone. Merely as examples, the pseudopeptide backbone may comprise any of an ethylglycine, a propylglycine, an ethyl-β-alanine, a propionyl linker, a retro inverso linker, a (S,S)-cyclohexyl linker, a (R,R)-cyclohexyl linker, an L-ornithine, a 2-me-ethyl-glycine, an ethyl-lysine, a L-proline, a n-proline, a glycine backbone/ethyl linker, a L-4-trans-amino proline, a L-4-cis-amino proline, a D-4-trans-amino proline, a β-alanine/proline, a glycylglycine/ethyl linker, a glycine/ethyl linker, a proline-glycine, a β-amino-alanine, E-OPA, Z-OPA, APNA, a serinol-ethyl-methyl linker, a serinol-ethyl-ethyl linker, an α-methyl-serinol-ethyl-ethyl linker, an aminopentan, a hydroxyethyl phosphono glycine, an aminoethyl phosphono glycine, a lysine, an aminoethyl prolyl or a serinyl methylene or combination thereof.

Further in accordance with the practice of the invention, the cell-penetrating polypeptide may be whole antibodies or derivatives thereof (e.g., fragments thereof (e.g., Fv, Fab', F(ab')$_2$) or recombinant proteins including recombinant variable regions of immunoglobulin molecules (e.g., scFv, bispecific antibody with scFv fragments)) containing the antigen binding domain and/or one or more complement determining regions of these antibodies that penetrate or are internalized into the cell upon or after binding. These cell-penetrating polypeptides can be from any source, e.g., rat, dog, cat, pig, horse, mouse or human. It is intended that the term "penetrate" or "internalize" means that the cell-penetrating polypeptide is taken into the cell. Further, some of the antibodies induce inhibition of cancer cell growth. The cell-penetrating polypeptide may be conjugated to a therapeutic agent.

In accordance with the practice of the invention, an antibody fragment includes at least a portion of the variable region of the immunoglobulin molecule that binds to its target, i.e., the antigen binding region. Some of the constant region of the immunoglobulin may also be included.

In an embodiment of the invention, cell penetration is dependent on a salvage pathway. For example, the nucleoside salvage pathway may be a pathway mediated by equilibrative nucleoside transporters (ENTs) or SLC29 family of integral membrane proteins. Examples of an equilibrative nucleoside transporter (ENT) or a member of the SLC29 family of integral membrane proteins is a transporter for purine and pyrimidine nucleosides and nucleobases or a metabolite thereof. The transporter for purine and pyrimidine nucleosides and nucleobases or a metabolite thereof may be an equilibrative nucleoside transporter ENT2.

In an embodiment of the invention, cell penetration is dependent on binding to a nucleic acid. In an embodiment of the invention, cell penetration is dependent on binding to DNA. In an embodiment of the invention, cell penetration is dependent on binding to an artificial DNA.

In an embodiment of the invention, cell penetration is mediated by an anti-DNA antibody, antibody fragment or derivative or variant which binds DNA and a cell surface molecule. In the case of the cell surface molecule, binding by the anti-DNA antibody, antibody fragment or derivative or variant to a cell surface molecule may either be direct or indirect binding. An example of a cell surface molecule is a cell surface polypeptide, carbohydrate, lipid, phospholipid, polycation or polyanion. An example of a polypeptide cell surface molecule is an equilibrative nucleoside transporter ENT2.

In an embodiment of the invention, cell penetration by the complex formed between the cell-penetrating polypeptide and DNA or its degradation product comprises cellular entry by the cell-penetrating polypeptide. The fate of the bound DNA or its degradation product is not known. The term "bind" in the phrase "to bind and penetrate the live cell" (or "to bind and penetrate additional live cells") by a complex comprising a cell-penetrating polypeptide and DNA or its degradation product refers to association of the complex with the live cell at the cell surface. The term "penetrate" in the above phrase refers to penetration of the cell by the cell-penetrating polypeptide; whereas, the fate of the DNA or its degradation product in the complex related to cell-penetration is not known and remains to be determined.

In one embodiment of the invention, following cell penetration, the anti-DNA antibody, antibody fragment or derivative or variant of the invention further penetrates or accumulates in the nucleus, e.g., 3E10 antibody.

Contemplated in the invention is the use of subcellular localization sequences linked to the cell-penetrating polypeptide of the invention so as to direct the cell-penetrating polypeptide to a desired cellular compartment following cell entry. Subcellular localization sequences are short polypeptides known in the art and may be linked to the cell-penetrating polypeptide by recombinant methods. Subcellular compartments which may be targeted with subcellular localization sequences include nucleus, nucleolus, cytoplasm, mitochondria, endoplasmic reticulum, Golgi, and peroxisome.

As used herein recombinant variable regions of immunoglobulin molecules refers to variable regions of Ig molecules which are produced by molecular biological means. Sequences encoding variable domain of the heavy and light chains may be isolated from T-cells, B-cells, leukemic cells, lymphoma cells, or immunoglobulin gene expressing cells, cloned into expression vector systems, and introduced into a host cell to produce "recombinant variable regions of immunoglobulin molecules." Alternatively, the sequences may be recombinantly produced or obtained from genomic DNA. Recombinant antibodies produced in this manner consists of an antibody or antibody fragment with the antigen binding specificity dependent on the variable region, comprising framework sequences and CDRs. Such recombinant antibodies may be formed from a polypeptide chain containing a variable region from a light chain and a polypeptide chain containing a variable region from a heavy chain or alternatively both the light chain and heavy chain variable regions could be found within a polypeptide in which a linker is used to link by recombinant DNA methods the coding sequences for the two variable chain regions, such as in the case of single chain Fv fragment (scFv).

When recombinant variable regions of immunoglobulin molecules are formed from two separate polypeptides, one for the light chain variable region and other for the heavy chain variable region, the recombinant Ig molecules may be an intact antibody as is normally produced by an organism from which the coding sequences were isolated or it could be a fragment. Antibody fragments could be produced either by recombinant DNA methods allowing tailored antibodies not dependent on specific protease cleavage sites or by proteolytic cleavage of the recombinant antibodies such as by IdeS, pepsin, or papain to produce Fab, F(ab') or F(ab')$_2$ fragments. The "recombinant variable regions of immunoglobulin molecules" may include the entire constant region or a portion of the constant region. In addition, the constant region of one antibody may be replaced by recombinant DNA method with the constant region of a different antibody if desired.

Single-chain antibodies or Fv consist of an antibody light chain variable domain or region ("$V_L$") and heavy chain variable region ("$V_H$") connected by a short peptide linker. The peptide linker allows the structure to assume a conformation which is capable of binding to antigen].

As used herein, a "conservative amino acid substitution" is the replacement of one amino acid with another of a similar type such that the binding specificity of the antibody is preserved. Amino acids of a similar type can be classified into several groups in which one amino acid within a group may be able to substitute for another member of the group:
(1) non-polar aliphatic amino acids, such as alanine, glycine, isoleucine, leucine and valine with alanine and glycine more related to each other and isoleucine, leucine and valine more related to each other based on size;
(2) neutral polar amino acids, such as serine, cysteine, threonine, glutamine and asparagine, and to a lesser extent methionine;
(3) cyclic amino acid, such as proline;
(4) aromatic amino acids, such as phenylalanine, tyrosine, and tryptophan;
(5) basic amino acids, such as histidine, lysine and arginine;
(6) acidic amino acids, such as aspartic acid, glutamic acid, asparagine and glutamine;
(7) aspartic acid and asparagine;
(8) glutamic acid and glutamine; and
(9) alanine, glycine, serine and cysteine Discussions of conservative amino acid substitution may be found in the patent literature.

Moreover, the present invention includes nucleic acids with silent mutation or silent mutations. A silent mutation is a mutation in the DNA which does not result in a change to the amino acid sequence of a protein or results in a change to the amino acid sequence of a protein but not its functionality. Degeneracy of the genetic code allows multiple codons to code for the same amino acid, allowing silent mutations to occur without changing the protein sequence. Such silent mutations are well-known and may be recited readily from publically available and accepted codon tables. In the case of silent mutations in which the amino acid sequence is changed but not the function of the protein, such silent mutations are generally mutations in which one amino acid of a certain chemical/physical characteristics is substituted with another of a similar type. Such mutations may involve conservative amino acid substitutions and may be detected through evolutionary changes but is best determine empirically.

The invention additionally provides a method for detecting an area or zone of cellular turnover. The method comprising (a) contacting cells at a potential area or zone of cellular turnover with a cell-penetrating polypeptide comprising 3E10 scFv or cell-penetrating determinants of a lupus autoantibody or a fragment or variant thereof so that the cell-penetrating polypeptide binds extracellular DNA present at an area or zone of cellular turnover; (b) permitting cellular uptake of the cell-penetrating polypeptide of (a) at the area or zone of cellular turnover; and (c) detecting the presence of the cell-penetrating polypeptide inside the cell body, thereby detecting an area or zone of cellular turnover.

In a further embodiment, the method further comprises identifying a center of cellular turnover wherein the center marked by presence of a lysed cell produces a gradient of extracellular DNA such that (a) presence of greatest amount of extracellular DNA near the center results in greatest uptake of the cell-penetrating polypeptide by live cells near the center of cellular turnover and (b) presence of lesser amount of extracellular DNA away from the center results in lower uptake of the cell-penetrating polypeptide by live cells away from the center of cellular turnover, thereby identifying the center of cellular turnover.

In accordance with the practice of the invention, the cells or tissue may be from a mammal or derived from a mammal. Examples of mammals include but are not limited to mouse, rat, hamster, cat, dog, rabbit, bovine, pig, sheep, goat, horse, monkey or human.

Cancer immunotherapy using anti-DNA antibodies, alone or combined with extracellular DNA, may follow the teachings generated from various approaches which have been successfully employed with respect to other types of cancer. For example, one way to apply antitumor monoclonal antibodies clinically is to administer them in unmodified form, using monoclonal antibodies of the invention which display antitumor activity and/or internalizing ability and/or in animal models. The anti-tumor activity of a particular anti-DNA mAb, or combination of anti-DNA mAbs, is preferably evaluated in vivo using a suitable animal model. Xenogenic cancer models, wherein human cancer explants or passaged xenograft tissues are introduced into immune compromised animals, such as nude or SCID mice, are particularly appropriate and are known. Examples of xenograft models of human prostate cancer (capable of recapitulating the development of primary tumors, micrometastasis, and the formation of osteoblastic metastases characteristic of late stage disease) are well known. The examples herein provide detailed experimental protocols for evaluating the antitumor potential of anti-DNA mAb preparations in vivo. Other in vivo assays are contemplated, such as those which measure regression of established tumors, interference with the development of metastasis, and the like.

The method of the invention contemplates the administration of single anti-DNA mAbs as well as combinations, or "cocktails", of different individual mAbs such as those recognizing different epitopes. Such mAb cocktails may have certain advantages inasmuch as they contain mAbs which bind to different epitopes and/or exploit different effector mechanisms or combine directly cytotoxic mAbs with mAbs that rely on immune effector functionality. Such mAbs in combination may exhibit synergistic therapeutic effects. In addition, the administration of anti-DNA mAbs may be combined with other therapeutic agents, including but not limited to various chemotherapeutic agents, androgen-blockers, and immune modulators. The anti-DNA mAbs may be administered in their "naked" or unconjugated form, or may have therapeutic agents conjugated to them.

The anti-DNA monoclonal antibodies used in the practice of the method of the invention may be formulated into pharmaceutical compositions comprising a carrier suitable for the desired delivery method. Suitable carriers include any material which when combined with the anti-DNA mAbs retains the anti-tumor function of the antibody or cytoprotective function of an antibody conjugate, if cytoprotective effect is desired, and is non-reactive with the subject's immune systems. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

The anti-DNA antibody formulations may be administered via any route capable of delivering the antibodies to the tumor site. Potentially effective routes of administration include, but are not limited to, intravenous, intraperitoneal, intramuscular, intratumoral, intradermal, and the like. The preferred route of administration is by intravenous injection. A preferred formulation for intravenous injection comprises the anti-DNA mAbs in a solution of preserved bacteriostatic water, sterile unpreserved water, and/or diluted in polyvinylchloride or polyethylene bags containing 0.9% sterile Sodium Chloride for Injection, USP. The anti-DNA mAb preparation may be lyophilized and stored as a sterile powder, preferably under vacuum, and then reconstituted in bacteriostatic water containing, for example, benzyl alcohol preservative, or in sterile water prior to injection.

Treatment may involve the repeated administration of the anti-DNA antibody preparation via an acceptable route of administration such as intravenous injection (IV), at an effective dose. Dosages will depend upon various factors generally appreciated by those of skill in the art, including without limitation the type of cancer and the severity, grade, or stage of the cancer, the binding affinity and half-life of the mAb or mAbs used, the extent of circulating shed DNA, the desired steady-state antibody concentration level, frequency of treatment, and the influence of chemotherapeutic agents used in combination with the treatment method of the invention. Typical daily doses may range from about 0.1 to 100 mg/kg. Doses in the range of 10-500 mg mAb per week may be effective and well tolerated, although even higher weekly doses may be appropriate and/or well tolerated. The principal determining factor in defining the appropriate dose is the amount of a particular antibody necessary to be therapeutically effective in a particular context. Repeated administrations may be required in order to achieve tumor inhibition or regression or, alternatively, cytoprotection if cytoprotection is desired. Initial loading doses may be higher. The initial loading dose may be administered as an infusion. Periodic maintenance doses may be administered similarly, provided the initial dose is well tolerated.

In another embodiment, the invention provides methods for selectively inhibiting a live cell by reacting any one or a combination of the immunoconjugates of the invention with the cell in an amount sufficient to inhibit the cell. Such amounts include an amount to kill the cell or an amount sufficient to inhibit cell growth or proliferation. As discussed supra the dose and dosage regimen will depend on the nature of the disease or disorder to be treated, its population, the site to which the antibodies are to be directed, the characteristics of the particular immunotoxin, and the patient. For example, the amount of immunoconjugate can be in the range of 0.1 to 200 mg/kg of patient weight.

In another embodiment, the invention provides a method for increasing uptake and enhancing efficacy of a cell-penetrating polypeptide comprising an anti-DNA antibody or a fragment or a variant thereof in targeting tumor or cancer cells comprising (a) inducing additional extracellular DNA release at or near the tumor or cancer cells through the use of a cell-damaging agent or introducing additional extracellular DNA or artificial DNA at or near the tumor or cancer cells; (b) administering the cell-penetrating polypeptide; (c) allowing the cell-penetrating polypeptide to form additional complexes with the additional extracellular DNA or artificial DNA; and (d) permitting the additional complexes in (c) to contact the tumor or cancer cells, thereby increasing uptake and enhancing efficacy of a cell-penetrating polypeptide comprising an anti-DNA antibody or a fragment or a variant thereof in targeting tumor or cancer cells.

In another embodiment, the invention provides a method for diagnosing or identifying a site of cell or tissue injury, an ischemic site with necrotic or apoptotic cells, a tumor site with necrotic or apoptotic cells, a cancer site with necrotic or apoptotic cells, or a site of cellular turnover comprising: (a) administering a cell-penetrating polypeptide comprising cell-penetrating determinants so as to interrogate one or more sites with the cell-penetrating polypeptide; (b) detecting the presence of the cell-penetrating polypeptide within the nucleus of a live cell; and (c) determining if a cluster of live cells with the cell-penetrating polypeptide is present at the interrogated sites, wherein presence of a cluster of live cells with the cell-penetrating polypeptide is indicative of a site of cell or tissue injury, an ischemic site with necrotic or apoptotic cells, a tumor site with necrotic or apoptotic cells, a cancer site with necrotic or apoptotic cells, or a site of cellular turnover, thereby, diagnosing or identifying a site of cell or tissue injury, an ischemic site with necrotic or apoptotic cells, a tumor site with necrotic or apoptotic cells, a cancer site with necrotic or apoptotic cells, or a site of cellular turnover.

In another embodiment, the invention provides a method for increasing or enhancing cytoprotection at an ischemic site comprising: (a) administering DNA to the site in an extracellular space so as to permit increased targeting of a cell-penetrating polypeptide comprising 3E10 scFv or cell-penetrating determinants of a lupus autoantibody or a fragment or variant thereof, and a cytoprotective agent; (b) administering the cell-penetrating polypeptide of (a); (c) contacting the extracellular DNA of (a) or its degradation product at an ischemic site with a cell-penetrating polypeptide of (a) so that the cell-penetrating polypeptide binds extracellular DNA or its degradation product at an ischemic site so as to form a complex; (d) contacting a live cell at risk for dying at an ischemic site with the complex in (c) so as to bind and penetrate the live cell; and (e) permitting additional complexes to form as in (c) and contacting additional live cells with said complexes so as to bind and penetrate additional live cells at risk for dying at an ischemic site; thereby, delivering additional cytoprotective agent to a cell at risk of dying and delivering cytoprotective agent to more cells at risk of dying at an ischemic site, thus, increasing or enhancing cytoprotection at an ischemic site.

In one embodiment, the cytoprotective agent is a heat shock protein, stress protein or chaperone protein. The heat shock protein, stress protein or chaperone protein may be any of Hsp-70, HspA1A, HspA1B, HspA1L, HspA2, HspA5, HspA6, HspA7, HspA8, HspA9, HspA12A, HspA12B, HspA13, HspA14, HspH1, HspH2, HspH3, and HspH4, Hsp40, DNAJA1, DNAJA2, DNAJA3, DNAJA4, DNAJB1, DNAJB2, DNAJB3, DNAJB4, DNAJB5, DNAJB6, DNAJB7, DNAJB8, DNAJB9, DNAJB11, DNAJB12, DNAJB13, DNAJB14, DNAJC1, DNAJC2, DNAJC3, DNAJC4, DNAJC5B, DNAJC5G, DNAJC6, DNAJC7, DNAJC8, DNAJC9, DNAJC10, DNAJC11, DNAJC12, DNAJC13, DNAJC14, DNAJC15, DNAJC16, DNAJC17, DNAJC18, DNAJC19, DNAJC20, DNAJC21, DNAJC22, DNAJC23, DNAJC24, DNAJC25, DNAJC26, DNAJC27, DNAJC28, DNAJC30, HSPB1, HSPB2, HSPB3, HSPB4, HSPB5, HSPB6, HSPB7, HSPB8, HSPB9, HSPB10, HSPB11, hsp90, hsp84, hsp27, hsp20, GRP78, alpha B crystallin, hsp60, hsp100, GRP94, GRP170, AIPL1, FKBP1A, FKBP1B, FKBP2, FKBP3, FKBP5, FKBP6, FKBP7, FKBP8, FKBP9, FKBP9L, FKBP10, FKBP11, FKBP12, FKBP14, FKBP15, FKBP38, FKBP52 and LOC541473.

In one embodiment, an ischemic site is associated with a condition selected from the group consisting of cardiac ischemia, myocardial infarction, ischemic colitis, mesenteric ischemia, brain ischemia, acute ischemic stroke, transient ischemic attack, vascular dementia, stroke, acute limb ischemia, cyanosis, gangrene, an embolism, a thrombosis, an atherosclerosis artery, a trauma, venous outflow obstruction, acute arterial ischemia, an aneurysm, mitral valve disease, chronic atrial fibrillation, cardiomyopathies, an occlusion, pulmonary embolus, acute arterial occlusion, peripheral arterial disease, a thromboembolism, a compression, a shearing, a laceration, arterial dissection, iatrogenic arterial injury, thoracic outlet syndrome, atherosclerosis, hypoglycemia, tachycardia, hypotension, septic shock, heart failure, superior mesenteric artery syndrome, sickle cell disease, induced g-force, frostbite, improper cold compression therapy, tourniquet application, increased glutamate receptor stimulation, arteriovenous malformation, peripheral artery occlusive disease, rupture of significant blood vessel, anemia, cardiac arrhythmia, cardiorespiratory arrest, subarachnoid hemorrhage, intracerebral hemorrhage, cerebral infarction, focal brain ischemia, global brain ischemia, pulmonary infarction, lung infarction, splenic infarction, limb infarction, deep vein thrombosis, phlebitis, skeletal muscle infarction, diabetes mellitus, avascular necrosis, testicular torsion, testicular infarction, central retinal artery infarction, sepsis, antiphospholipid syndrome, giant-cell arteritis, hemia, volvulus, hepatic ischemia, dehydration and infection.

Compositions

The invention provides a pharmaceutical composition comprising an anti-DNA antibody, fragment or derivative or variant thereof and, optionally, a suitable carrier. The invention also provides a composition or pharmaceutical composition comprising a cell-penetrating polypeptide which comprises cell-penetrating determinants and extracellular DNA or artificial DNA. The invention also provides a composition or pharmaceutical composition comprising a cell-penetrating polypeptide which comprises cell-penetrating determinants and extracellular DNA or artificial DNA, and optionally, a suitable carrier. The antibody or fragment or derivative or variant thereof may be conjugated or linked to a therapeutic drug or a cytotoxic agent. The antibody or fragment or derivative or variant thereof may be conjugated or linked to a hapten, an epitope tag or an imaging agent. The antibody or fragment or derivative thereof may be conjugated or linked to a cytoprotective agent. The antibody or fragment or derivative thereof may be conjugated or linked to a chemical compound, a peptide or a protein.

Suitable carriers for pharmaceutical compositions include any material which when combined with the nucleic acid or other molecule of the invention retains the molecule's activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods. Such compositions may also be formulated within various lipid compositions, such as, for example, liposomes as well as in various polymeric compositions, such as polymer microspheres.

Anti-DNA Antibodies

The invention provides anti-DNA antibodies for use in the methods and compositions of the invention. In one embodiment, the anti-DNA antibodies which may be used in the invention includes any of H7 Antibody, H9 Antibody, H72 Antibody, H205 Antibody, H317 Antibody F14-6 Antibody, SN22 Antibody, SN50 Antibody, SN111 Antibody, SN112 Antibody, SN575 Antibody, SN604 Antibody, Sn608 Antibody, F4.1 Antibody, J20.8 Antibody, F14.6 Antibody, and 9D7 antibody or a derivative or variant thereof (Vlahakos D, Foster Mh, Ucci Aa, Barrett Kj, Datta Sk, And Madaio Mp (1992) "Murine Monoclonal Anti-Dna Antibodies Penetrate Cells, Bind To Nuclei, And Induce Glomerular Proliferation And Proteinuria In Vivo." J. Am. Soc. Nephrol. 2(8):1345-54; Ruíz-ArgUelles A, Pérez-Romano B, Llorente L, Alarcón-Segovia D, And Castellanos Jm (1998) "Penetration Of Anti-DNA Antibodies Into Immature Live Cells." J. Autoimmun. 11(5):547-56; Avrameas A, Ternynck T, Nato F, Buttin G, And Avrameas S (1998) "Polyreactive Anti-Dna Monoclonal Antibodies And A Derived Peptide As Vectors For The Intracytoplasmic And Intranuclear Translocation Of Macromolecules" Proc. Natl. Acad. Sci. U.S.A. 95(10): 5601-5606; Song Yc, Sun Gh, Lee Tp, Huang Jc, Yu Cl, Chen Ch, Tang Sj, And Sun Kh (2008) "Arginines In The CDR Of Anti-dsDNA Autoantibodies Facilitate Cell Internalization Via Electrostatic Interactions." Eur. J. Immunol. 38(11):3178-90). Sequence Of CDR For F4.1 Antibody, J20.8 Antibody And F14.6 Antibody May Be Found In Avrameas A, Ternynck T, Nato F, Buttin G, And Avrameas S (1998) "Polyreactive Anti-DNA Monoclonal Antibodies And A Derived Peptide As Vectors For The Intracytoplasmic And Intranuclear Translocation Of Macromolecules" Proc. Natl. Acad. Sci. U.S. A. 95(10):5601-5606. Sequence Of CDR For 9d7 Antibody May Be Found In Song Yc, Sun Gh, Lee Tp, Huang Jc, Yu Cl, Chen Ch, Tang Sj, And Sun Kh (2008) "Arginines In The CDR Of Anti-DsDNA Autoantibodies Facilitate Cell Internalization Via Electrostatic Interactions." Eur. J. Immunol. 38(11):3178-90. In One Embodiment, The Anti-DNA Antibodies Which May Also Be Used In The Invention Includes 5c5 Monoclonal Antibody, 5c6 Monoclonal Clonal Antibody And 4h2 Monoclonal Antibody (Weisbart Rh, Et Al., J. Immunol. 1990 144(7): 2653-2658; Zack Dj, Et Al., J. Immunol. 1995 154(4): 1987-1994; Weidle Uh, Et Al., Cancer Genomics Proteomics 2013 10: 239-250; Weisbart Rh, Et Al., Sci. Rep. 2015 5: 12022; Noble Pw, Et Al., Sci. Rep. 2014 4:5958; Colburn Kk, Et Al., J. Rheumatol. 2003 30(5):993-7).

3E10 Antibodies

The invention further provides an example of an anti-DNA antibody which is a 3E10 antibody (e.g., polyclonal, monoclonal, chimeric, and humanized antibodies) for use in the methods and compositions of the invention. Anti-3E10 antibodies that are particularly contemplated include monoclonal ntibodies as well as fragments thereof (e.g., recombinant proteins, such as scFv) containing the antigen binding domain and/or one or more complement determining regions of these antibodies. 3E10 Mab is a murine monoclonal antibody and its nucleic acid sequence and amino acid sequence provided in: FIGS. 3 and 4 Of Zack Dj, Et Al., J. Immunol. 1995 154(4): 1987-1994; FIGS. 3 And 4 Of Us Patent Application Publication No.: US 2008/0292618 A1; FIGS. 1 and 2 of PCT International Publication No.: WO 2010/138769 A1, published 2 Dec. 2010; GenBank Accession Numbers: L16982 for mAb 3E10 Vh chain and L34051 for mAb 3E10 vic light chain. location of the complement-determining regions (e.g., CDR1, CDR2 and CDR3) Along With The Framework Regions (i.e., FR1, FR2, FR3, and FR4) of the 3E10 variable heavy chain and light chain domains are provided in FIGS. 3 and 4 of Zack Dj, Et Al., J. Immunol. 1995 154(4): 1987-1994; FIGS. 3 and 4 of US Patent Application Publication No.: US 2008/0292618 A1; FIGS. 1 and 2 of PCT International Publication No. WO 2010/138769 A1, published 2 Dec. 2010. In a preferred embodiment, the anti-3E10 antibody or its fragment is a variant, such as the D31N 3E10 variant in which amino acid residue 31 of 3E10 variable heavy chain is mutated from an aspartic acid (D) to an asparagine (N). This D31N variant of 3E10 antibody has increased binding to ssDNA And dsDNA (Zack Dj, Et Al., *J. Immunol.* 1995 154(4): 1987-1994) and enhanced cell and nuclear penetration (Zack Dj, Et Al., *J. Immunol.* 1996 157(5): 2082-2088; Weisbart Wh, et al., J. Autoimmunity 1998 11(5): 539-546). In an embodiment of the invention, the 3E10 antibody or its fragment or variant is a derivative. In another embodiment, a derivative may be in the form of an immunoconjugate. Such immunoconjugates are discussed supra.

Humanized Antibodies

The present invention encompasses humanized antibodies. Various methods for humanizing non-human antibodies are known in the art.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art.

Human Antibodies

Human antibodies of the invention can be constructed by combining Fv clone variable domain sequences selected from human-derived phage display libraries with known human constant domain sequences. Alternatively, human monoclonal antibodies of the invention can be made by the hybridoma method. Human myeloma and mouse-human heteromyeloma cell lines for the production of human monoclonal antibodies are well known in the art. Gene shuffling can also be used to derive human antibodies from non-human, where the human antibody has similar affinities and specificities to the starting non-human antibody using a method called epitope imprinting.

Bispecific Antibodies

Bispecific antibodies are monoclonal, preferably human or humanized, antibodies that have binding specificities for at least two different antigens. Bispecific antibodies may be obtained from intact antibodies or antibody fragments. Methods for making bispecific antibodies are known in the art and described herein. Antibodies with more than two valencies are contemplated. For example, trispecific antibodies can be prepared.

Antibody Variants

In some embodiments, amino acid sequence modifications of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made. Where the antibody comprises an Fc region, the carbohydrate attached thereto may be altered. Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. For example, in one preferred embodiment of the 3E10 antibody, amino acid residue 31 of 3E10 variable heavy chain is mutated from an aspartic acid (D) to an asparagine (N) to produce the D31N variant of 3E10 antibody. This D31N variant of 3E10 antibody has increased binding to ssDNA and dsDNA (Zack D J, et al., *J. Immunol.* 1995 154(4): 1987-1994) and enhanced cell and nuclear penetration (Zack D J, et al., *J. Immunol.* 1996 157(5): 2082-2088; Weisbart W H, et al., *J. Autoimmunity* 11(5): 539-546).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Antibody Derivatives

The antibodies of the present invention can be further modified to contain additional proteinaceous or nonproteinaceous moieties that are known in the art. Proteinaceous or nonproteinaceous moieties include, but are not limited to, chemical functional groups such as hydrophilic linkers (e.g. polyethylene glycol), crosslinking agents, metal chelators, epitope tags, peptides such as AGIH tetrapeptide sequence, cytotoxic agents, enzymes, cytoprotective agents, a second antibody (or fragment or variant thereof), imaging agents or detectable markers. Suitable examples of the imaging agent or detectable marker include a radioisotope, a fluorophore, a fluorescent quencher, an enzyme, a luminescent compound, a chemiluminescent compound, a bioluminescent compound, a photon emitter, a heavy metal, a ferromagnetic agent, a contrast agent, a metal chelator, and an epitope.

For example, derivatives of anti-DNA antibodies of the invention (such as 3E10 antibody) may be a fusion protein comprising the cell-penetrating determinants of the anti-DNA antibody (such as 3E10 antibody) and a second biologically active desired functional protein or peptide.

Nucleic Acid Molecules

In an embodiment, the invention provides a nucleic acid molecule encoding the anti-DNA antibodies in the compositions of the invention. The nucleic acid molecule may encode the anti-DNA antibodies in the compositions of the invention.

The nucleic acids of the invention may comprise nucleotide sequences and polypeptides encoding amino acid sequences which are at least about 70% identical, preferably at least about 80% identical, more preferably at least about 90% identical and most preferably at least about 95% identical (e.g., 95%, 96%, 97%, 98%, 99%, 100%) to the reference nucleotide and amino acid sequences of the present invention (i.e., see example herein) when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference amino acid sequences of the present invention when the comparison is performed with a BLAST algorithm wherein the parameters of the algorithm are selected to give the largest match between the respective sequences over the entire length of the respective reference sequences, are also included in the present invention.

The nucleic acid molecule may be a DNA molecule (e.g., cDNA) encoding the bispecific composition of the invention. For example, the invention provides for a DNA construct comprising a vector that expresses the bispecific composition of the invention.

Additionally, the invention provides a vector which comprises the nucleic acid molecule of the invention. The host vector system comprises the vector of the invention in a suitable host cell. Examples of suitable host cells include but are not limited to bacterial cell and eukaryotic cells.

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Immunoconjugates

The invention also provides immunoconjugates (interchangeably termed "antibody-drug conjugates" or "ADC"), comprising any of the anti-DNA antibodies described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). Immunoconjugates may also comprise any of the anti-DNA antibodies described herein conjugated to a cytoprotective agent such as a heat shock protein, stress protein or chaperone protein.

Chemotherapeutic agents useful in the generation of immunoconjugates are described herein. Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein. Other antitumor agents that can be conjugated to the antibodies of the invention include BCNU, streptozoicin, vincristine and 5-fluorouracil. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *saponaria officinalis* inhibitor, gelonin, mitogellin, restrictocin, phenomycin, enomycin and the tricothecenes.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In an embodiment, heat shock protein, stress protein or chaperone protein include any of Hsp-70, HspA1A, HspA1B, HspA1L, HspA2, HspA5, HspA6, HspA7, HspA8, HspA9, HspA12A, HspA12B, HspA13, HspA14, HspH1, HspH2, HspH3, and HspH4, Hsp40, DNAJA1, DNAJA2, DNAJA3, DNAJA4, DNAJB1, DNAJB2, DNAJB3, DNAJB4, DNAJB5, DNAJB6, DNAJB7, DNAJB8, DNAJB9, DNAJB11, DNAJB12, DNAJB13, DNAJB14, DNAJC1, DNAJC2, DNAJC3, DNAJC4, DNAJC5B, DNAJC5G, DNAJC6, DNAJC7, DNAJC8, DNAJC9, DNAJC10, DNAJC11, DNAJC12, DNAJC13, DNAJC14, DNAJC15, DNAJC16, DNAJC17, DNAJC18, DNAJC19, DNAJC20, DNAJC21, DNAJC22, DNAJC23, DNAJC24, DNAJC25, DNAJC26, DNAJC27, DNAJC28, DNAJC30, HSPB1, HSPB2, HSPB3, HSPB4, HSPB5, HSPB6, HSPB7, HSPB8, HSPB9, HSPB10, HSPB11, hsp90, hsp84, hsp27, hsp20, GRP78, alpha B crystallin, hsp60, hsp100, GRP94, GRP170, AIPL1, FKBP1A, FKBP1B, FKBP2, FKBP3, FKBP5, FKBP6, FKBP7, FKBP8, FKBP9, FKBP9L, FKBP10, FKBP11, FKBP12, FKBP14, FKBP15, FKBP38, FKBP52 and L00541473.

Immunoconjugate of any anti-DNA antibody described herein and a cytoprotective agent may be produced by any coupling method known in the art, including chemical crosslinking and recombinant methods.

The antibody or fragment thereof of the invention may be labeled with a detectable marker or conjugated to a second molecule, such as a therapeutic agent (e.g., a cytotoxic agent or cytoprotective agent) thereby resulting in an immunoconjugate. For example, the therapeutic agent includes, but is not limited to, an anti-tumor drug, a toxin, a radioactive agent, a cytokine, a second antibody, an enzyme, a substrate, a heat shock protein, a stress protein or a chaperone protein. Further, the invention provides an embodiment wherein the antibody of the invention is linked to an enzyme that converts a prodrug into a cytotoxic drug. The invention provides an embodiment wherein the antibody of the invention is linked to an enzyme that participates in a denatured protein response or protein refold. The invention provides an embodiment wherein the antibody of the invention is linked to substrate that participates in a detoxification process or an enzyme that detoxifies, such as glutathione S-transferase, cytochrome P450 oxidase, UDP-glucuronosyltransferase or alcohol dehydrogenase.

Examples of cytotoxic agents include, but are not limited to ricin, ricin A-chain, doxorubicin, daunorubicin, taxol, ethidium bromide, mitomycin, etoposide, tenoposide, vincristine, vinblastine, colchicine, dihydroxy anthracenedione, actinomycin D, diphtheria toxin, *Pseudomonas* exotoxin (PE) A, PE40, abrin, abrin A chain, modeccin A chain, alpha-sarcin, gelonin, mitogellin, restrictocin, phenomycin, enomycin, curcin, crotin, calicheamicin, *saponaria officinalis* inhibitor, maytansinoids, and glucocorticoid and other chemotherapeutic agents, as well as radioisotopes such as $^{212}$Bi, $^{131}$I, $^{131}$In, $^{90}$Y, and $^{186}$Re. Suitable detectable markers include, but are not limited to, a radioisotope, a fluorescent compound, a bioluminescent compound, chemiluminescent compound, a metal chelator or an enzyme. Antibodies may also be conjugated to an anti-cancer pro-drug activating enzyme capable of converting the pro-drug to its active form.

Additionally, the recombinant protein of the invention comprising the antigen-binding region of any of the monoclonal antibodies of the invention can be used to treat cancer. In such a situation, the antigen-binding region of the recombinant protein is joined to at least a functionally active portion of a second protein having therapeutic activity. The second protein can include, but is not limited to, an enzyme, lymphokine, oncostatin, toxin or a second antibody directed to a different antigen. Suitable toxins include those described above.

Techniques for conjugating (e.g., by chemical means) or joining (by recombinant means) therapeutic agents to antibodies are well known (see, e.g., Amon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); and Thorpe et al., "The Preparation And Cytotoxic Properties Of Antibody-Toxin Conjugates", *Immunol. Rev.*, 62:119-58 (1982)).

Pharmaceutical Formulations

Therapeutic formulations comprising an antibody of the invention are prepared for storage by mixing the antibody having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended. In one embodiment, the formulation contains an anti-DNA antibody or fragments, derivatives or variants thereof, as described herein and DNA (extracellular DNA) as the only therapeutic agents in the formulation.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy 20th edition (2000).

The formulations to be used for in vivo administration must be sterile. This is readily accomplished by filtration through sterile filtration membranes. When appropriate, chemical or radiation sterilization method may be used.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In one embodiment, the sustained-release formulation comprises a cell-penetrating polypeptide and a carrier. In another embodiment, the sustained-release formulation comprises a cell-penetrating polypeptide and a preservative. In another embodiment, the sustained-release formulation comprises DNA and/or its degradation product(s) and a carrier. In another embodiment, the sustained-release formulation comprises DNA and/or its degradation product(s) and a preservative. In one embodiment, the sustained-release formulation comprises a cell-penetrating polypeptide and DNA and/or its degradation products. In one embodiment, the sustained-release formulation comprises a cell-penetrating polypeptide and DNA and/or its degradation products and a carrier. In one embodiment, the sustained-release formulation comprises a cell-penetrating polypeptide and DNA and/or its degradation products. In one embodiment, the sustained-release formulation comprises a cell-penetrating polypeptide and DNA and/or its degradation products and a preservative.

The formulation may be an immediate-release formulation. In one embodiment, the immediate-release formulation comprises a cell-penetrating polypeptide and a carrier. In another embodiment, the immediate-release formulation comprises a cell-penetrating polypeptide and a preservative.

In another embodiment, the immediate-release formulation comprises DNA and/or its degradation product(s) and a carrier. In another embodiment, the immediate-release formulation comprises DNA and/or its degradation product(s) and a preservative. In one embodiment, the immediate-release formulation comprises a cell-penetrating polypeptide and DNA and/or its degradation products. In one embodiment, the immediate-release formulation comprises a cell-penetrating polypeptide and DNA and/or its degradation products and a carrier. In one embodiment, the immediate-release formulation comprises a cell-penetrating polypeptide and DNA and/or its degradation products. In one embodiment, the immediate-release formulation comprises a cell-penetrating polypeptide and DNA and/or its degradation products and a preservative.

In a further embodiment, the formation is a combination of an immediate-release formulation and a sustained-release formulation.

Use of immunologically reactive fragments, such as the Fab, Fab', or F(ab)$_2$ fragments or scFv is often preferable, especially in a therapeutic context, as these fragments are generally less immunogenic than the whole immunoglobulin. Further, bi-specific antibodies specific for two or more epitopes may be generated using methods generally known in the art. Further, antibody effector functions may be modified so as to enhance the therapeutic effect of 3E10 antibodies on cancers. Homodimeric antibodies may also be generated by cross-linking techniques known in the art (e.g., Wolff et al., Cancer Res. 53: 2560-2565). The invention also provides pharmaceutical compositions having the monoclonal antibodies or anti-idiotypic monoclonal antibodies of the invention, such as anti-idiotypic mAb 1C7 directed against anti-DNA antibody including 3E10 mAb (Weisbart R H et al., J. Immunol. 1990 144(7): 2653-2658). Such anti-idiotypic antibodies may be useful in neutralizing activity of an anti-DNA antibody or 3E10 antibody or a fragment, variant or derivative thereof.

The following examples are intended to illustrate the present invention, not to limit the scope of the invention in any way.

EXAMPLE 1

Methods and Materials

Production and Purification of 3E10 scFv. 3E10 scFv used in these studies was previously modified by a D31N mutation in CDR1 of the variable region of the heavy chain that results in a 50-fold increase in DNA-binding affinity and efficiency of nuclear penetration. 3E10 scFv was produced in *P. pastoris* and purified as described previously (10).

Cell Lines and Tissue Culture. The GM02605 human fibroblast cell line (Coriell Biorepository, Camden, N.J.) was selected for these studies because it grows to confluence in 96-well tissue culture plates with remarkably high viability (>99% viability maintained over several days of growth as determined by propidium iodide exclusion assay). Cells were grown in MEM with 10% FCS and washed with MEM without serum before incubation with 10 μM 3E10 scFv for one hour. Nuclear penetration by 3E10 scFv was then examined by anti-Myc immunostaining as previously described (10).

Cell Lysate. COS-7 cell lysate was prepared by subjecting cells to multiple freeze-thaw cycles in liquid nitrogen. Cell debris was removed by centrifugation. DNA-depleted COS-7 cell lysate was prepared by passing the lysate through a Centricon cellulose filter with a molecular weight cut off of 10,000 Da.

DNA. Purified calf thymus DNA sheared to an average length of 2000 bp was purchased from Invitrogen (Ultrapure, Invitrogen, Carlsbad, Calif.).

Human Glioma Xenografts. U87 human glioma subcutaneous xenografts were generated in nude mice. When tumors reached size of 100 mm$^3$ mice were treated with intraperitoneal injection (IP) of control PBS buffer or 0.8 mg 3E10 scFv in PBS. Mice were sacrificed 4 or 24 hours after treatment, and tumors and selected normal tissues were fixed in formalin and embedded in paraffin. Tissues were then surveyed for nuclear penetration by 3E10 scFv by immunohistochemistry (IHC) as previously described (11). Briefly, sections were incubated with 9E10 anti-Myc (Invitrogen) primary antibody directed at the C-terminal Myc tag in 3E10 scFv before probing with secondary antibody and visualizing with 3,3'-diaminobenzidine and counterstaining with hematoxylin.

Results

A Factor Released by Dead Cells Appears to Enhance Nuclear Penetration by 3E10 scFv. We sought to test the efficiency of nuclear penetration by 3E10 scFv into cells in the absence of extracellular DNA, and for these studies selected the GM02605 human fibroblast cell line because it maintains a high degree of viability (>99%) with minimal cell death even while maintained in culture for several days. With low rates of turnover the confounding effects of DNA released by dead cells are minimized. The GM02605 cells were washed with serum free media and then treated with 10 μM 3E10 scFv for one hour, after which cells were fixed and immunostained for presence of the fragment. Remarkably, 3E10 scFv did not penetrate into most cells. Instead, 3E10 scFv was detected only in the nuclei of cells centered around what appeared to be a dead cell, with a gradient effect observed with diminishing amounts of intranuclear antibody detected with increasing distance from the central dead cell. A representative image demonstrating this effect is shown in FIG. 1. This observation was consistent with a factor released locally by dying cells enhancing nuclear penetration of 3E10 scFv into surrounding cells.

Addition of Cell Lysate Promotes Homogenous Nuclear Uptake of 3E10 scFv. To test the hypothesis that a factor released by dead cells enhances nuclear uptake of 3E10 scFv we next compared the efficiency of nuclear penetration of the fragment into the GM02605 fibroblasts in the presence or absence of a cell lysate. As shown in FIG. 2, in the absence of the cell lysate minimal nuclear uptake of 3E10 scFv was observed. However, the addition of cell lysate facilitated nuclear penetration by 3E10 scFv into ~100% of the cells. These results further support the hypothesis that a factor released by dead cells contained in cell lysate promotes nuclear uptake of 3E10 scFv.

DNA-Depleted Cell Lysate does not Enhance Nuclear Uptake of 3E10 scFv. Based on our previous observations that 3E10 scFv binds DNA and is unable to penetrate cells that are deficient in the ENT2 nucleoside transporter, we hypothesized that DNA is the critical factor in cell lysate that promotes nuclear uptake of 3E10 scFv. To test this, the GM06205 fibroblasts were treated with 10 μM 3E10 scFv in the presence of cell lysate that had been filtered to remove DNA content. In contrast to the complete cell lysate, the DNA-depleted lysate did not enhance nuclear uptake of 3E10 scFv (FIG. 2), which strongly supports the hypothesis that DNA is the relevant factor contributing to nuclear penetration by the fragment.

Addition of Purified DNA Promotes Homogeneous Nuclear Uptake of 3E10 scFv. To confirm that extracellular DNA enhances nuclear penetration by 3E10 scFv, we next treated the GM02605 fibroblasts with 3E10 scFv in the presence of purified DNA. As shown in FIG. 2, addition of purified DNA to the media significantly enhanced the efficiency of penetration by 3E10 scFv into cell nuclei. Taken together, these data indicate that nuclear penetration by 3E10 scFv is enhanced by the presence of extracellular DNA.

3E10 scFv Targets Tumor Cells In Vivo. Based on the observation that 3E10 scFv penetrates cell nuclei most efficiently in the presence of extracellular DNA, we hypothesized that when administered in vivo the fragment would accumulate most efficiently into tissues in which there would be expected to be a higher concentration of extracellular DNA due to high cellular turnover, such as is associated with tumors. To test this, subcutaneous U87 human glioma xenografts were generated in immunodeficient mice, and once tumors grew to size of 100 mm$^3$ mice were treated with intraperitoneal injection of control buffer or 3E10 scFv. Mice were then sacrificed 4 or 24 hours after treatment, and tumors and select normal tissues were immunostained for the presence of 3E10 scFv. As shown in FIG. 3A, four hours after treatment 3E10 scFv was detected in the nuclei of the U87 xenograft cells, but was not detected in tissues of major organs including heart, kidney, skeletal muscle, and liver. 3E10 scFv was also detected in the tumors 24 hours after treatment, demonstrating the stability of the uptake into tumor nuclei (FIG. 3B). These results are consistent with enhanced uptake of 3E10 scFv into sites of high cell turnover where DNA is released from dying cells.

Discussion

3E10 scFv has been explored as a therapeutic intracellular transport system and has successfully mediated delivery of p53, Hsp70, and the anti-MDM2 antibody 3G5 to target tissues in vivo. In addition, 3E10 by itself has been shown to sensitize tumors in vivo to DNA-damaging agents including ionizing radiation and doxorubicin. Importantly, 3E10 and 3E10 scFv have never been found to be significantly toxic to any normal tissues in any of these previous in vivo studies. The present study was carried out to further evaluate preliminary evidence that 3E10 scFv preferentially targets ischemic tissue or areas of high cell turnover rates such as malignant tissue. For example, we previously found that the Fv-Hsp70 fusion protein protected rats from reperfusion injury of ischemic brain even when administered 3 hours after ligation of the middle cerebral artery, and in this study 3E10 scFv was shown to localize in ischemic but not normoxic brain (9). These findings were consistent with a previous study that showed targeting of an anti-histone antibody to an area of cell death in vivo (12). We also observed that the 3E10-3G5 bispecific antibody yielded a profound suppression of MDM2-addicted tumors in vivo but showed a remarkable absence of systemic toxicity (13), suggesting a preferential localization of the agent to tumor cells.

In the present study we have now shown that penetration of 3E10 scFv into live cells in vitro requires the presence of extracellular DNA. Of note, our findings are consistent with a previous report that demonstrated the requirement of extracellular DNA for penetration of an another anti-DNA antibody into living T-cells, however only 10% of cells internalized antibody (14). Moreover, when 3E10 scFv was administered systemically it was observed to preferentially localize into U87 cancer cells implanted subcutaneously, consistent with the fact that rapidly growing cancers are ischemic and have a high level of cell turnover and therefore the local environment should be enriched for extracellular DNA. The selective targeting of 3E10 scFv to such tissues may therefore explain in part the remarkable lack of off-target toxicity of 3E10 alone and of 3E10 scFv-p53 and 3E10-3G5 administered systemically in our previous studies.

We previously showed that 3E10 scFv penetrates living cells through the ENT2 nucleoside salvage pathway, and our results here suggest that 3E10 scFv bound to DNA may be processed by membrane nucleases and phosphatases into fragments that are accessible to this pathway. Further studies are required to characterize these membrane-related events, but the primary significance of our study is the demonstration that 3E10 scFv has targeting specificity in vivo to areas of tissue ischemia and high cell turnover. This finding further establishes the potential to use 3E10 scFv in a variety of clinical applications that include protecting organs from reperfusion injury and cytotoxic applications for cancer therapy. In addition, recognition of the requirement for extracellular DNA for nuclear penetration by 3E10 scFv suggests that combinations of 3E10 scFv with targeted approaches that selectively increase cell turnover in tumors, such as locally applied radiotherapy, might facilitate the subsequent penetration of 3E10 scFv into all cells comprising a tumor mass due to enhanced release of DNA by dying cells.

REFERENCES

1. Alarcon-Segovia, D. (2001) Antinuclear antibodies: to penetrate or not to penetrate, that was the question. *Lupus* 10, 315-318
2. Zack, D. J., Stempniak, M., Wong, A. L., Taylor, C., and Weisbart, R. H. (1996) Mechanisms of cellular penetration and nuclear localization of an anti-double strand DNA autoantibody. *J. Immunol.* 157, 2082-2088
3. Hansen, J. E., Fischer, L. K., Chan, G., Chang, S. S., Baldwin, S. W., Aragon, R. J., Carter, J. J., Lilly, M., Nishimura, R. N., Weisbart, R. H., and Reeves, M. E. (2007) Antibody-mediated p53 protein therapy prevents liver metastasis in vivo. *Cancer Res.* 67, 1769-1774
4. Hansen, J. E., Sohn, W., Kim, C., Chang, S. S., Huang, N. C., Santos, D. G., Chan, G., Weisbart, R. H., and Nishimura, R. N. (2006) Antibody-mediated Hsp70 protein therapy. *Brain Res.* 1088, 187-196
5. Weisbart, R. H., Hansen, J. E., Chan, G., Wakelin, R., Chang, S. S., Heinze, E., Miller, C. W., Koeffler, P. H., Yang, F., Cole, G. M., Min, Y. S., and Nishimura, R. N. (2004) Antibody-mediated transduction of p53 selectively kills cancer cells. *Int. J. Oncol.* 25, 1867-1873
6. Weisbart, R. H., Hansen, J. E., Nishimura, R. N., Chan, G., Wakelin, R., Chang, S. S., Baresi, L., and Chamberlain, J. S. (2005) An intracellular delivery vehicle for protein transduction of micro-dystrophin. *J. Drug Target.* 13, 81-87
7. Hansen, J. E., Chan, G., Liu, Y., Hegan, D. C., Dalal, S., Dray, E., Kwon, Y., Xu, Y., Xu, X., Peterson-Roth, E., Geiger, E., Gera, J., Sweasy, J. B., Sung, P., Rockwell, S., Nishimura, R. N., Weisbart, R. H., and P, M. G. (2012) Targeting cancer with a lupus autoantibody. *Science translational medicine* 4, 157ra142
8. Hansen, J. E., Tse, C. M., Chan, G., Heinze, E. R., Nishimura, R. N., and Weisbart, R. H. (2007) Intranuclear protein transduction through a nucleoside salvage pathway. *J. Biol. Chem.* 282, 20790-20793
9. Zhan, X., Ander, B. P., Liao, I. H., Hansen, J. E., Kim, C., Clements, D., Weisbart, R. H., Nishimura, R. N., and Sharp, F. R. (2010) Recombinant Fv-Hsp70 protein mediates neuroprotection after focal cerebral ischemia in rats. *Stroke* 41, 538-543
10. Weisbart, R. H., Wakelin, R., Chan, G., Miller, C. W., and Koeffler, P. H. (2004) Construction and expression of a bispecific single-chain antibody that penetrates mutant p53 colon cancer cells and binds p53. *Int. J. Oncol.* 25, 1113-1118
11. Yang, X. R., Charette, L. A., Garcia-Closas, M., Lissowska, J., Paal, E., Sidawy, M., Hewitt, S. M., Rimm, D. L., and Sherman, M. E. (2006) Construction and validation of tissue microarrays of ductal carcinoma in situ and terminal duct lobular units associated with invasive breast carcinoma. *Diagn. Mol. Pathol.* 15, 157-161
12. Chen, F. M., Epstein, A. L., Li, Z., and Taylor, C. R. (1990) A comparative autoradiographic study demonstrating differential intratumor localization of monoclonal antibodies to cell surface (Lym-1) and intracellular (TNT-1) antigens. *J. Nucl. Med.* 31, 1059-1066
13. Weisbart, R. H., Gera, J. F., Chan, G., Hansen, J. E., Li, E., Cloninger, C., Levine, A. J., and Nishimura, R. N. (2012) A cell-penetrating bispecific antibody for therapeutic regulation of intracellular targets. *Molecular cancer therapeutics* 11, 2169-2173
14. Okudaira, K., Yoshizawa, H., and Williams, R. C., Jr. (1987) Monoclonal murine anti-DNA antibody interacts with living mononuclear cells. *Arthritis Rheum.* 30, 669-678

What is claimed is:

1. A method for selectively targeting live cells at a site of interest with a cell-penetrating polypeptide, the method comprising:
    (a) introducing an isolated DNA near or around the live cells at the site of interest;
    (b) administering the cell-penetrating polypeptide comprising cell-penetrating determinants, before, after or concurrently with the DNA of step (a);
    (c) contacting the DNA or its degradation product with the cell-penetrating polypeptide so that the cell-penetrating polypeptide binds the DNA or its degradation product near or around the live cells so as to form a complex;
    (d) contacting one of the live cells with the complex in (c) so as to bind and penetrate the live cell; and
    (e) permitting additional complexes to form as in (c) and contacting additional cells with said complexes so as to bind and penetrate additional live cells at the site of interest;
    wherein introducing an isolated DNA near or around the live cells at the site of interest is or comprises administration of the isolated DNA at the site of interest by injection, microinjection, microprojectile or implantation or a combination thereof, or alternatively, implantation of an object or substance containing DNA or artificial DNA, wherein the implant releases DNA or artificial DNA in a single burst or over an extended period; thereby, selectively targeting live cells at the site of interest with a cell-penetrating polypeptide, wherein the cell-penetrating polypeptide is a 3E10 antibody or a fragment thereof, wherein the fragment is a single chain Fv (scFv) fragment of mAb 3E10 antibody.

2. A method for inhibiting a tumor associated with ischemia, cellular/tissue necrosis or cellular/tissue apoptosis by selective targeting of live cells at a site of interest by the method of claim 1.

3. The method of claim 1, wherein the anti-DNA antibody binds single-stranded DNA, double-stranded DNA or both.

4. The method of claim 1, wherein the 3E10 antibody has a binding specificity of an antibody as produced by a hybridoma having ATCC accession number PTA 2439 or a fragment thereof.

5. The method of claim 1, wherein cell penetration is dependent on a salvage pathway.

6. The method of claim 5, wherein the salvage pathway is a nucleoside salvage pathway mediated by equilibrative nucleoside transporters (ENTs) or SLC29 family of integral membrane proteins.

7. The method of claim 6, wherein the equilibrative nucleoside transporter (ENT) or a member of the SLC29 family of integral membrane proteins is an equilibrative nucleoside transporter ENT2.

8. The method of claim 1, wherein the cells are present in a mammal or derived from a mammal.

9. The method of claim 1, wherein the cell-penetrating polypeptide is or comprises a therapeutic agent.

10. The method of claim 1, wherein the 3E10 antibody is a humanized variant of an antibody produced by the hybridoma having ATCC accession number PTA 2439.

11. The method of claim 1, wherein the 3E10 antibody, the fragment of the mAb 3E10 antibody, or the single chain Fv (scFv) fragment of the mAb 3E10 antibody is joined to an amino acid sequence AGIH at its amino terminus.

12. The method of claim 1, wherein the 3E10 antibody, the fragment of the mAb 3E10 antibody or the single chain Fv (scFv) fragment of the mAb 3E10 antibody has a change in its amino acid sequence, wherein the change in the amino acid sequence enhances cell penetration and comprises an amino acid substitution in the 3E10 variable heavy chain at amino acid 31 from an aspartic acid to an asparagine (D31N).

13. The method of claim 1, wherein the isolated DNA is single-stranded, double-stranded, triple-stranded, or four-stranded or a combination thereof, comprising a phosphodiester bond, a phosphorothioate bond or a methylphosphonate bond or a combination thereof or an artificial DNA comprising a pseudopeptide backbone, comprising an ethylglycine, a propylglycine, an ethyl-β-alanine, a propionyl linker, a retro inverso linker, a (S,S)-cyclohexyl linker, a (R,R)-cyclohexyl linker, an L-ornithine, a 2-me-ethyl-glycine, an ethyl-lysine, a L-proline, a n-proline, a glycine backbone/ethyl linker, a L-4-trans-amino proline, a L-4-cis-amino proline, a D-4-trans-amino proline, a P-alanine/proline, a glycylglycine/ethyl linker, a glyeine/ethyl linker, a proline-glycine, a f3-amino-alanine, E-OPA, Z-OPA, APNA, a serinol-ethyl-methyl linker, a serinol-ethyl-ethyl linker, an α-methyl- serinol-ethyl-ethyl linker, an aminopentan, a hydroxyethyl phosphono glycine, an aminoethyl phosphono glycine, a lysine, an aminoethyl prolyl or a serinyl methylene or a combination thereof.

14. The method of claim 1, wherein the cell-penetrating polypeptide further comprises a cytotoxic agent selected from the group consisting of a chemotherapeutic agent, a drug, a growth inhibitory agent, a toxin and a radioactive isotope.

15. The method of claim 1, wherein the cell penetrating polypeptide further comprises a cytoprotective agent selected from the group consisting of a heat shock protein, stress protein and chaperone protein.

16. The method of claim 1, wherein the cell-penetrating polypeptide is further linked or bound to an imaging agent or detectable marker.

17. The method of claim 16, wherein the imaging agent or detectable marker is selected from the group consisting of a radioisotope, a fluorophore, a fluorescent quencher, an enzyme, a luminescent compound, a chemiluminescent compound, a bioluminescent compound, a photon emitter, a heavy metal, a ferromagnetic agent, a contrast agent, a metal chelator, and an epitope.

18. The method of claim 1, wherein the mAb 3E10 antibody, the fragment of the mAb 3E10 antibody, or the single chain 17v (scFv) fragment of the mAb 3E10 antibody is a humanized antibody or fragment from a hybridoma having ATCC accession number PTA 2439.

19. The method of claim 1, wherein the site of interest is an injury site.

20. The method of claim 19, wherein the injury site is an intracranial injury, brain injury, myocardial infarction, skin injury, liver injury, gastrointestinal injury, lung injury, eye injury, kidney injury, pancreas injury, peritoneal injury, bone injury, nasopharyngeal injury, uterine injury, cervical injury, breast injury, organ injury, tissue injury, burn or radiation injury.

* * * * *